(12) United States Patent
Nakaji

(10) Patent No.: US 10,925,525 B2
(45) Date of Patent: Feb. 23, 2021

(54) COMBINED PULSE OXIMETRY AND DIFFUSING WAVE SPECTROSCOPY SYSTEM AND CONTROL METHOD THEREFOR

(71) Applicant: CANON U.S.A. INC., Melville, NY (US)

(72) Inventor: Haruo Nakaji, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 484 days.

(21) Appl. No.: 15/680,760

(22) Filed: Aug. 18, 2017

(65) Prior Publication Data
US 2019/0053745 A1 Feb. 21, 2019

(51) Int. Cl.
| | |
|---|---|
| *A61B 5/1455* | (2006.01) |
| *A61B 5/00* | (2006.01) |
| *A61B 5/053* | (2006.01) |
| *A61B 5/026* | (2006.01) |

(52) U.S. Cl.
CPC ........ *A61B 5/14551* (2013.01); *A61B 5/0066* (2013.01); *A61B 5/0075* (2013.01); *A61B 5/0261* (2013.01); *A61B 5/053* (2013.01); *A61B 5/4881* (2013.01); *A61B 5/7282* (2013.01); *A61B 5/725* (2013.01); *A61B 5/7207* (2013.01); *A61B 5/7214* (2013.01)

(58) Field of Classification Search
None
See application file for complete search history.

(56) References Cited

U.S. PATENT DOCUMENTS

| | | | |
|---|---|---|---|
| 4,911,167 A * | 3/1990 | Corenman | A61B 5/02416 600/324 |
| 6,037,579 A | 3/2000 | Chan et al. | |
| 6,076,010 A | 6/2000 | Boas et al. | |
| 6,611,339 B1 | 8/2003 | Yang et al. | |
| 6,754,518 B1 | 6/2004 | Lloyd et al. | |
| 6,831,741 B1 | 12/2004 | De Kruif et al. | |
| 7,130,671 B2 | 10/2006 | Baker, Jr. et al. | |
| 8,320,981 B1 | 11/2012 | Mayer et al. | |
| 8,463,346 B2 | 6/2013 | Kuhn et al. | |
| 8,649,838 B2 | 2/2014 | Chen et al. | |
| 8,692,990 B2 | 4/2014 | Matousek | |
| 8,772,039 B2 | 7/2014 | Nadkarni | |

(Continued)

FOREIGN PATENT DOCUMENTS

| | | |
|---|---|---|
| CN | 103169480 A | 6/2013 |
| KR | 20160053281 A | 5/2016 |
| WO | 2015109005 A1 | 7/2015 |

OTHER PUBLICATIONS

"Signal Extraction Technology", Technical Bulletin 1, Masimo Corporation, 2006; pp. 1-12.

(Continued)

*Primary Examiner* — Marjan Fardanesh
(74) *Attorney, Agent, or Firm* — Canon U.S.A, Inc., IP Division

(57) ABSTRACT

A system comprises of a pulse oximeter and diffusing wave spectroscopy (DWS) apparatus to perform pulse oximetry measurements. To calculate oxygen saturation, the pulse oximeter utilizes a pulse wave which is measured by an apparatus other than the pulse oximeter itself. In one embodiment, the different apparatus mentioned above is the diffusing wave spectroscopy (DWS) apparatus.

19 Claims, 13 Drawing Sheets

(56) References Cited

U.S. PATENT DOCUMENTS

| | | | |
|---|---|---|---|
| 8,792,757 | B2 | 7/2014 | Boudoux et al. |
| 8,810,796 | B2 | 8/2014 | Hays et al. |
| 8,838,213 | B2 | 9/2014 | Tearney et al. |
| 9,179,843 | B2 | 11/2015 | Moghaddam et al. |
| 2012/0184831 | A1 | 7/2012 | Seetamraju et al. |
| 2014/0206980 | A1 | 7/2014 | Lee et al. |
| 2015/0276571 | A1 | 10/2015 | Hajjarian et al. |
| 2016/0345880 | A1* | 12/2016 | Nakaji ............... A61B 5/14552 |
| 2016/0361017 | A1 | 12/2016 | Busch, Jr. et al. |

OTHER PUBLICATIONS

Astorga, "Haemoglobin Sensing with Optical Spectroscopy During Minimally Invasive Procedures", http://discovery.ucl.ac.uk/1461729/1/RdPSA_vf_comp.pdf; Department of Medical Physics and Biomedical Engineering, University College London; University of London; 2014; pp. 1-180.

Boas, D. et al., "Spatially varying dynamical properties of turbid media probed with diffusing temporal light correlation"; J. Opt. Soc. Am. A, vol. 14, No. 1; Publication [online]. January ; pp. 192-215, 1997.

Boas, David A., "Handbook of Biomedical Optics, Near-Infrared Diffuse Correlation Spectroscopy for Assessment of Tissue Blood Flow", Chapter 10_CRC Press, 2011; pp. 195-216.

Buckley, E. et al., "A Novel Combined Frequency-Domain Near-Infrared Spectroscopy and Diffuse Correlation Spectroscopy System", in Biomedical Optics 2014, OSA Technical Digest (online) (Optical Society of America, 2014), paper BM3A.17; pp. 1-3.

Carp, SA et al., "Validation of Optical Measurements of Cerebral Blood Flow and volume with SPION and ASL fMRI: Implications for CMRO2 Changes During Hypercapnia"; Proc. Intl. Soc. Mag. Reson. Med. 17 (2009); p. 1626.

D. J. Pine, et al., "Diffusing-Wave Spectroscopy", Phys. Rev. Letters., vol. 60, No. 12, pp. 1134-1137, Mar. 21, 1988.

T. Durduran, et al., "Diffuse optics for tissue monitoring and tomography". Reports on Progress in Physics, 2010. 73(7): 43; pp. 1-87.

G. Dietsche, et al., "Fiber-based multispeckle detection for time-resolved diffusing-wave spectroscopy: characterization and application to blood flow detection in deep tissue", Appl. Opt., vol. 46, No. 35, pp. 8506-8514, 2007.

"International Symposium on Metabolic Imaging and Spectroscopy"; Perelman School of Medicine at the University of Pennsylvania, Jun. 18-19, 2013, pp. 1-89.

Irwin et al., "Influence of tissue absorption and scattering on diffuse correlation spectroscopy blood flow measurements", Biomed. Opt. Exp., vol. 2, No. 7, pp. 1969-1985, published Jun. 17, 2011.

Gerd Keiser, et al., "Review of Diverse Optical Fibers Used in Biomedical Research and Clinical Practice", http://biomedicaloptics.spiedigitallibrary.org/article.aspx?articleid=1901514; Review of diverse optical fibers used in biomedical research and clinical practice, Journal of Biomedical Optics, SPIE, pp. 1-46.

He Lian, et al., "Using optical fibers with different modes to improve the signal-to-noise ratio of diffuse correlation spectroscopy flow-oximeter measurements", Journal of Biomedical Optics, vol. 18(3), 037001, Mar. 2013, pp. 1-11.

Bernard Widrow et al., "Adaptive noise cancelling: principles and applications", Proc. IEEE, 63(12), pp. 1692-1716, Dec. 1975.

Wang et al., "Fast blood flow monitoring in deep tissues with real-time software correlators", Biomedical Optics Express, vol. 7, No. 3, Mar. 1, 2016; pp. 776-797.

T. Durduran, et al., "Does the photon-diffusion coefficient depend on absorption?", Journal of the Optical Society of America A, Dec. 1997, pp. 3358-3365. vol. 14, Issue 12.

* cited by examiner

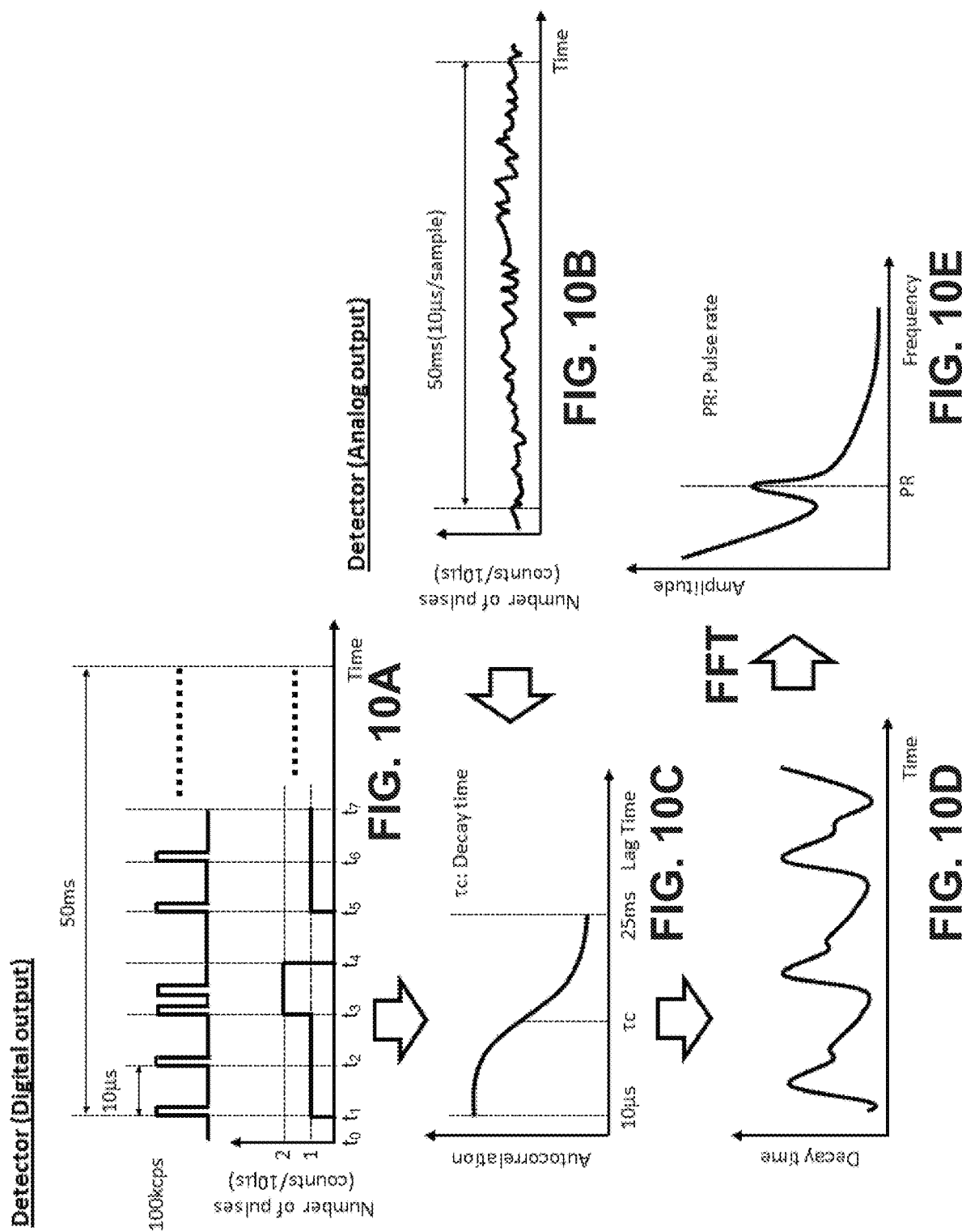

COMBINED PULSE OXIMETRY AND DIFFUSING WAVE SPECTROSCOPY SYSTEM AND CONTROL METHOD THEREFOR

BACKGROUND

Field

The disclosure of this patent application relates generally to optical imaging, and in particular it relates to an integrated device including a pulse oximeter and a diffusing wave spectroscopy (DWS) apparatus, and control methods therefor.

Related Art

Pulse oximetry instruments are widely known and commonly used for monitoring oxygen levels and other parameters of live tissue in a non-invasive manner. Oxygen saturation ($SO_2$) is a measure of the oxygen being carried by hemoglobin in blood, and it can be defined as the ratio of the concentration of hemoglobin in its oxygenated state to that of the total hemoglobin content (i.e., the total of hemoglobin in oxygenated and deoxygenated states). Therefore, $SO_2 = [HbO_2/(HbO_2+Hb)]$, where $HbO_2$ is hemoglobin in its oxygenated state (oxyhemoglobin) and Hb is hemoglobin in its deoxygenated state (deoxyhemoglobin).

A pulse oximeter monitors oxygen saturation of tissue by taking advantage of the fact that oxygenated hemoglobin and deoxygenated hemoglobin absorb light at different wavelengths. This difference in optical absorption characteristics of hemoglobin also allows pulse oximetry to measure other blood flow parameters, such as the blood flow volume caused by individual blood pulsations, and/or the rate of blood pulsations corresponding to each heartbeat of a patient. In fact, the "pulse" in pulse oximetry refers to the time-varying amount of arterial blood circulating during each cardiac cycle of the heart.

FIG. 1A (reproduced from non-patent literature (NPL) document entitled "Pulse Oximetry", by Amal Jubran, Critical Care (2015) 19:272, herein referred as "NPL Reference 1") shows the typical absorption spectra of oxyhemoglobin ($HbO_2$) and reduced hemoglobin or deoxyhemoglobin (Hb). It can be seen from FIG. 1A that, in general, when the wavelength is shorter than around 800 nanometers (nm), the absorption coefficient of deoxyhemoglobin is higher than that of oxyhemoglobin, and when the wavelength is longer than around 800 nm, the absorption coefficient of deoxyhemoglobin (reduced hemoglobin in FIG. 1A) is lower than that of oxyhemoglobin. Therefore, pulse oximeters measure oxygen saturation using light sources having at least two different wavelengths. Of the at least two wavelengths used in a pulse oximetry, one wavelength located in a range lower than about 800 nm (e.g., 660 nm) and another wavelength located in a range higher than about 800 nm (e.g., 940 nm) are generally used. Typical light sources are monochromatic light emitting diodes (LEDs) or semiconductor laser sources Conventional pulse oximetry therefore measures the differential optical density of red and infrared light intensities as transmitted through (or reflected from) tissue, and calculates a ratio of the optical densities. Utilizing the optical density ratio, an arterial oxygen saturation ($SaO_2$) value is empirically calculated based on the ratio of optical densities. Therefore, oxygen saturation $SO_2$ tells the percentage (%) of the total hemoglobin that is carrying oxygen. Normal values of arterial oxygen saturation can reach values over 95%.

However, these values may vary due to various factors including, but not limited to, lack of oxygen supply, ventilation deficiencies, or disease. Therefore, accurate monitoring of oxygen saturation levels in human tissue is extremely important in assessing the health status of an individual.

FIG. 1B (also reproduced from NPL Reference 1) shows waveforms of signals that can be observed in a pulse oximeter. The first (A) waveform is a normal signal which can be observed when the signal is pulsed by only the heat beat. The second (B) waveform is a signal which can be observed when perfusion is low. In the third (C) waveform can be observed when a noise signal is mixed into the normal signal; this represents a noise artifact. The fourth (D) waveform illustrates a distortion due to patient's motion; this represents a motion artifact. If a noise signal is added to a normal signal like in the third (C) waveform, or a motion artifact is added to a normal signal like in the fourth (D) waveform, it becomes difficult to measure the pulse wave and pulse rate accurately. Also, a measurement error may become larger because of low signal-to-noise ratio.

In order to solve the above issues, various conventional techniques have been proposed. For example, U.S. Pat. No. 7,130,671 describes a system that employs an adaptive comb filter (ACF) to track the varying heart rate to digitally comb filter the pulsating absorbance signal. To remove noise energy, the comb filter frequency varies as the heart rate varies, attenuating motion energy not at the heart rate or multiples thereof. In this manner, only the energy at integer multiples of the heart rate are allowed through the filter. The filtered data is then processed through various algorithms.

As another example, a medical technology company named Masimo, from Irvine Calif., has developed a pulse oximetry technique named Masimo Signal Extraction Technology (SET). According to Masimo SET, the venous blood is considered as the most significant contributor to noise during motion. Therefore, to reduce or eliminate such noise, Masimo SET establishes a "noise reference" corresponding to the venous component, and then uses an adaptive noise canceller (ANC) to cancel the contribution of the venous component.

The procedure for determining the arterial oxygen saturation by using Masimo SET® processing is as follows: (1) Sweep all optical density ratios that correspond to oxygen saturations of 1% to 100%. (2) Compute the reference signal (noise) for each optical density ratio. (3) Measure the output power of the adaptive noise canceller for each reference signal. (4) Identify an appropriate peak in the discrete saturation transform (DST) that corresponds to the arterial oxygen saturation (largest $SpO_2$ value). From the above, if at (4) there are two or more peaks, it is postulated that the peak with the highest optical density ratio is the artery oxygen saturation. This is described in "Signal Extraction Technology", Technical Bulletin 1, Masimo Corporation, 2006 (referred herein as "NPL Reference 2").

As described above, therefore, it is conventional practice to measure the arterial pulsation signal based on light absorption principles, and to use signal processing or filtering techniques to limit the effects of noise and motion artifacts. These conventional techniques assume that the optical path length of arterial blood flow is pulsed by the heartbeat and that the optical path length of blood flow through other than the artery (i.e., the optical path length of tissue and veins) is not pulsed.

Diffusing wave spectroscopy (DWS), also called diffuse correlation spectroscopy (DCS) has been recently used for diagnosis of tissues. DWS can measure the motion of moving particles in media by using laser speckle principles.

In the field of medical devices, DWS is utilized for monitoring blood flow (blood flow rate) in tissue. A laser with long coherence length is employed in a DWS system because light is scattered multiple times as it is diffused through the tissue. A photon counting detector (typically and avalanche photodiode) is used for detecting the diffused light because single speckle grain is detected, and the detected intensity is very weak. An autocorrelation function is calculated by a correlator. The decay time of the autocorrelation function curve is related to the change in blood flow.

By combining a pulse oximeter and DWS technology, it has been shown that oxygen metabolism of tissue can be calculated. For example, U.S. Pat. No. 8,082,015 describes a technique for measuring blood flow rate and oxygenation characteristics of tissue, and determining oxygen metabolism of the tissue as a function of the measured blood flow rate and measured oxygenation. The blood flow rate characteristics are measured as a function of light fluctuations caused by the tissue, while the oxygenation characteristics are measured as a function of transmission of light through the tissue (absorption) with respect to the wavelength of light.

SUMMARY

The inventors herein have determined that there is a significant difference between obtaining the arterial pulsation signal based on light absorption principles alone versus obtaining the arterial pulsation signal based on light diffusion principles. Therefore, to address the above described shortcomings of conventions pulse oximetry technology, the inventors herein disclose systems and methods of using light diffusion principles to measure the arterial pulsation signal. Compared to obtaining the arterial pulsation signal based on light absorption alone, a more robust and exact arterial pulsation signal can be obtained using light diffusion principles even if the pulse oximeter signal is noisy, and even if motion artifacts are included in the signal detected by the pulse oximeter.

The various embodiments disclosed in the present patent application describe a novel integrated device comprised of a pulse oximeter and a pulse wave measuring apparatus to improve pulse oximetry measurements. Notably, according to the present disclosure, the pulse oximeter utilizes a pulse wave which is measured by the pulse wave measuring apparatus which is an apparatus other than the pulse oximeter itself. In one embodiment, the pulse wave measuring apparatus mentioned above is a diffusing wave spectroscopy (DWS) apparatus. A DWS apparatus is more sensitive to optical scattering than to optical absorption. This allows the integrated oximeter/DWS device to be more sensitive to light diffusion and less susceptive to noise and motion artifacts.

According to one aspect of the present application, an integrated device includes a part for irradiating light beams of different wavelengths from a plurality of light sources to a tissue sample, a part for collecting light of the different wavelengths transmitted through the sample and delivering the collected light to a plurality of optical detectors, and a processor for quantifying intensities of the collected light detected at each of the different wavelengths and for calculating an autocorrelation function and its decay time from light intensity fluctuations detected at one of the wavelengths diffused through the sample. The processor calculates oxygen saturation from the intensities of lights detected by the optical detectors, and calculates blood flow from light intensity fluctuations.

In some embodiments, light diffused through the sample is collected using a single double clad fiber which is in optical communication with the plurality of optical detectors. In this case, collected light of the plurality of wavelengths propagates through both the core and the inner cladding of the double clad fiber. Optical and spatial filters are used for dividing by wavelength and dividing spatially the light which propagates in the core of the double clad fiber from the light beam which propagates in the inner cladding of the double clad fiber.

Further features and advantageous of the invention will become apparent to those skilled in the art from the following description of exemplary embodiments with reference to the attached drawings.

BRIEF DESCRIPTION OF DRAWINGS

FIGS. 10A, 10B, 10C, 10D and 10E are graphical plots used to explain a process of detecting a pulse wave using DWS principles.

DETAILED DESCRIPTION

Figure 1A:
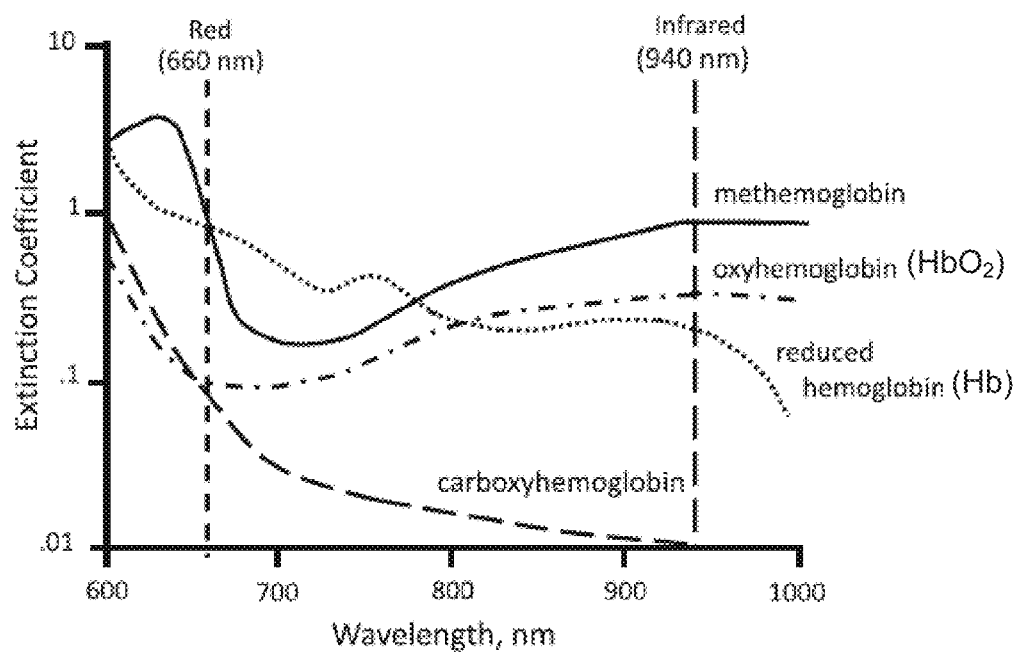
FIG. 1A illustrates a hemoglobin absorption graph.
Figure 1B:
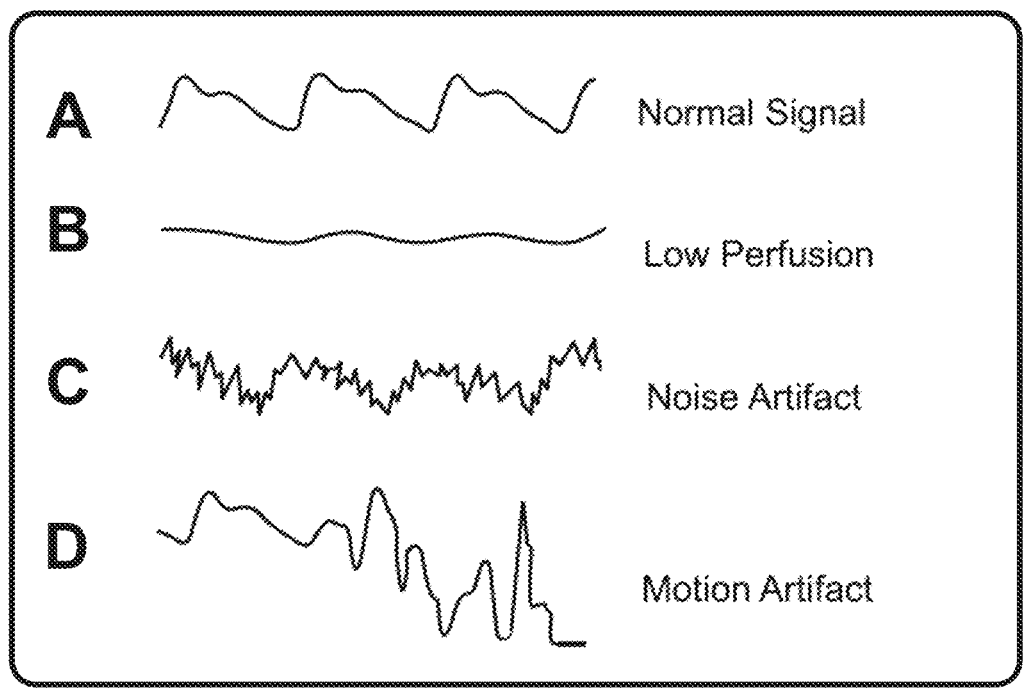
FIG. 1B illustrates typical signals that may be observed in a pulse oximeter.

In the following description, reference is made to the accompanying drawings which are illustrations of embodiments in which the disclosed invention may be implemented and practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail as not to unnecessarily lengthen the present disclosure. Some embodiments of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage devices such as a magnetic or optical disk and disk drive for storing information and instructions, an optional user output device such as a display device (e.g., a monitor) for displaying information to a user, an optional user input device including alphanumeric and function keys (e.g., a keyboard) for communicating information and command selections to the processor, and an optional user input device such as a pointing device (e.g., a mouse) for communicating user input information and command selections to the processor.

As will be appreciated by those skilled in the art, the present examples may be embodied as a system, method or computer program product stored in tangible media. Accordingly, some examples may take the form of an entirely hardware embodiment, an entirely software embodiment (including firmware, resident software, micro-code, etc.) or an embodiment combining software and hardware aspects that may all generally be referred herein as a "circuit", "module" or "system". Further, some embodiments may take the form of a computer program product embodied in any non-transitory tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that when executed by a computer or other programmable data processing apparatus causes the computer or processing apparatus to function in a particular manner, such that the instructions stored in the computer-readable media constitute an article of manufacture including instructions and processes which implement the function/act/step specified in the flowchart and/or block diagram.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without departing from structural or functional meaning.

Exemplary embodiments are described below in more detail with reference to the several drawings where like reference numerals refer to like parts. Various embodiments of a combined system having a pulse oximeter and DWS apparatus are described below. Notably, according to the present disclosure, in order to calculate oxygen saturation more accurately, a pulse oximeter utilizes a pulse wave which is measured by an apparatus other than the pulse oximeter itself. In one embodiment, the different apparatus is a diffusing wave spectroscopy (DWS) apparatus.

Figure 2A:
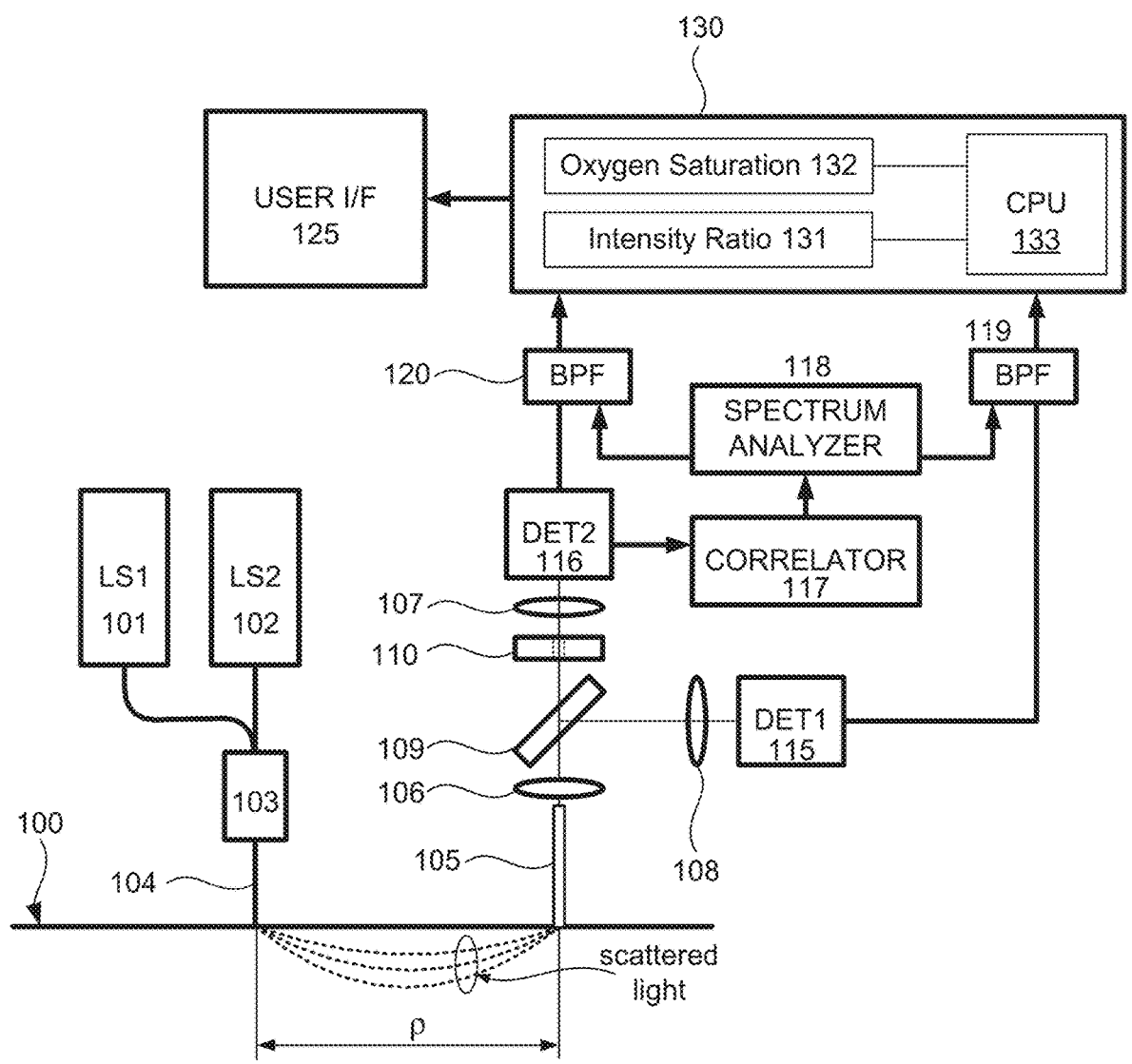
FIG. 2A illustrates a hybrid system combining a pulse oximeter and DWS apparatus.

FIG. 2A shows a system having a pulse oximeter and DWS apparatus. The DWS apparatus is an example of a pulse wave measurement apparatus. In the system of FIG. 2A, two source-detector pairs are formed by two light sources and two detectors. The sources include a first light source 101 (LS1) and a second light source 102 (LS2), and the detectors include a first detector 115 (DET1) and a second detector 116 (DET2). In this embodiment, the wavelengths of light sources 101 and 102 are 660 nm and 910 nm, respectively. The coherence length of the second light source 102 at the wavelength of 910 nm is equal to or longer than the coherence length of the first light source 101 at the wavelength of 660 nm. Light sources 101 and 102 can be implemented as individual semiconductor laser sources (laser diodes) each generating the desired wavelength. Alternatively, at least one of the light sources can be implemented by a light emitting diode (LED), and the other light source may be implemented by a semiconductor laser. For example, a near-infrared LED having wavelength of 660 nm may be used as light source 101 (LS1), and an infrared semiconductor laser having wavelength of 910 nm may be used as light source 102 (LS2). The detectors 115 and 116 may be implemented as individual avalanche photodiodes (APDs), as separated arrays of APDs, as a photo multiplier tube (PMT), or similar photon counting photodetectors.

As discussed above, conventional pulse oximetry measures absorption intensities of two or more lights having different wavelengths, and calculates a ratio thereof to then derive oxygen saturation values. In the present embodiment, the light of both wavelengths is attenuated by static and dynamic absorbers on its path from the light sources 101-102, through the patient's body (sample 100), to the light detectors 115-116. The light detectors 115-116 receive the attenuated light intensities of the two wavelengths transmitted through the patient's body (sample 100). Then, the signals output from the detectors 115-116 are amplified, filtered by electronic band-pass filters 119-120, converted from analog to digital signals, and further processed in a microprocessor system (computer 130).

Computer 130, in conjunction with a correlator 117 and spectrum analyzer 118, uses a pulse finding algorithm (refer to FIGS. 10A-10E) to analyze the received signals for identifying the peaks of a pulse wave signal and for determining the pulse period. After identifying the pulse period, the computer 130 derives therefrom the relative absorption ratios using an intensity ratio calculation unit 131. Subsequently, the computer 130 calculates the arterial oxygen saturation value using an oxygen saturation calculation unit 132. To calculate accurate oxygen saturation values and other parameters related thereto, the computer 130 may use the relative absorption ratios and calibration data based on extinction coefficients from the absorption spectrum of hemoglobin and oxyhemoglobin at the appropriate wavelengths.

More specifically, as mentioned before, the arterial blood whose quantity varies synchronously with the time of the patient's heartbeat represents the primary dynamic absorber during the pulse period. All other absorbers, such as venous blood, skin, tissue or bone, are considered to be not time-variant. Therefore, according to the various embodiments of the present invention, detection and analysis of the pulse wave is not based on absorption principles alone, but instead the pulse wave is analyzed and its pulse characteristics is confirmed based on light diffusion principles. Analyzing the pulse wave according to light diffusion principles is considered advantageous because light diffusion is more susceptible to time-varying events, and less affected by noise and movement artifacts than light absorption.

In FIG. 2A, the second detector 116 provides a pulse wave signal based on optical diffusion principles and a correlator 117 and spectrum analyzer 118 are used to accurately detect pulse parameters of the pulse wave. This will be explained more in detail further below.

Continuing to refer to FIG. 2A, a single mode fiber (SMF) is attached to each light source 101 and 102. The two light beams which are output from the light sources 101 and 102 are combined by a wavelength combiner 103 (e.g., a fiber coupler), and the combined light beams are input to one single mode fiber 104. Examples of wavelength combiners can be found in U.S. Pat. No. 8,792,757. The combined light beams are irradiated onto the sample 100 (e.g., tissue of a human subject) at a predetermined point or region of interest (ROI). Absorbers in the sample 100 (e.g., red blood cells (RBCs), organelles, etc.) scatter the two light beams multiple times within the sample as the light diffuses through the sample. At least part of each multiple scattered light beam is collected by a double-clad fiber (DCF) 105 at a distance ρ away from the irradiation point.

The reason for collecting the scattered light with a double-clad fiber is as follows. When the light which is scattered multiple times in the patient's body (e.g., tissue sample 100) is collected by optical fibers, both single mode and multi mode fibers could be used. In this regard, since the core diameter of multi mode fibers (MMFs) is larger than the core diameter of single mode fibers (SMFs), a MMF would be suitable as a detection fiber for a pulse oximeter to be able to measure absorption more appropriately. However, in diffusing wave spectroscopy (DWS) where light diffusion is better measured by detecting only a single speckle grain (a single photon) at a time, a single-mode fiber or a few-modes fiber is considered to be more appropriate. Therefore, logic dictates that a SMF for the DWS apparatus and a MMF for the pulse oximeter should be used as detection fibers in a hybrid oximeter/DWS system. In that case, however, there will be an increase in the number of fibers and optical connectors, as well as an increase on the cost, for connecting the combined oximeter/DWS system probe to a console. As a solution, to reduce the number of fibers and optical connectors and thus minimize fabrication costs and potential anomalies, the inventors herein propose to use in the combined (hybrid) oximeter/DWS system a SMF for delivering the light from the light sources to the sample, and a common DCF for collecting the transmitted light of both the pulse oximeter and DWS apparatus.

Figure 2B:
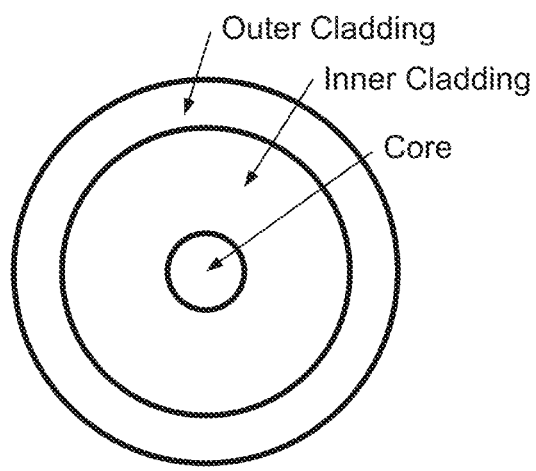
FIG. 2B illustrates details of a double-clad fiber.

A view of the cross-sectional structure of an exemplary DCF 105 is shown in FIG. 2B. The DCF 105 comprises a core surrounded by an inner cladding, which in turn is surrounded by an outer cladding. As an example, a DCF having a core of 5 μm diameter and 0.12 numerical aperture (NA), an inner cladding of 130 μm diameter and 0.16 NA, may be used in the combined (hybrid) oximeter/DWS system for collecting the light transmitted through the sample. The collected light beams propagate in both the core and the inner cladding of DCF 105. As shown in FIG. 2A, a dichroic mirror 109 can be used for split the light beams transmitted through DCF 105 according to wavelength characteristics of the dichroic mirror. The dichroic mirror 109 is an example of a wavelength splitter for separating the light transmitted through the DCF 105. As another example, a double-clad fiber coupler/splitter may be used.

Figure 2C:
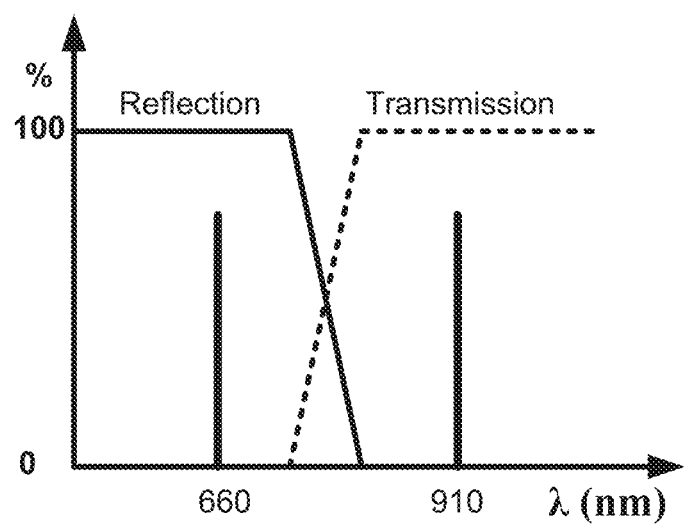
FIG. 2C illustrates spectral characteristics of a dichroic filter applicable to the system of FIG. 2A.

FIG. 2C illustrates transmission and reflection characteristics of the dichroic mirror 109 according to its wavelength characteristics. As illustrated in the graph of FIG. 2C, dichroic mirror 109 is configured to transmit light having 910 nm wavelength, and to reflect light having 660 nm wavelength. Naturally, it will be a matter of design choice to use a different dichroic mirror 109 having different wavelength characteristics, e.g., having reversed reflection and transmission characteristics, or having entirely different wavelengths for transmission and reflection.

Referring again to FIG. 2A, the light that is collected by the DCF 105 passes through a collimating lens 106. At the dichroic mirror 109, the light of 660 nm wavelength is reflected by the dichroic mirror 109 and input into the first detector (DET1) 115 via a lens 108; and the light of 910 nm wavelength is transmitted through the dichroic mirror 109, guided though a pinhole 110, and then focused by a lens 107 on the second detector 116 (DET2). The light beams which travel in the inner cladding of DCF 105 are blocked by the pinhole 110, and therefore light beams which travel in the inner cladding of DCF 105 do not arrive at second detector 116. In this manner, the intensity of light of 660 nm wavelength is detected by the first detector 115, and the intensity of light of 910 nm wavelength is detected by the second detector 116. The pinhole 110 is an example of a spatial filter, while the dichroic mirror 109 is an example of an optical filter.

A signal output from the second detector 116 is input to a correlator 117 in order to calculate the decay time of an autocorrelation function generated therein. A spectrum analyzer 118 measures the power spectrum of the autocorrelation function and detects peaks of the power spectrum of a time-series signal (pulse wave signal) output from the correlator 117.

Filters 119 and 120 are electronic bandpass filters which serve to filter the signal output from detectors 115 and 116, respectively. The center frequency of bandpass filters 119 and 120 is optimized based on the peak detected by spectrum analyzer 118. The electronic bandpass filter 119 filters an intensity signal output from the first detector 115, and the electronic bandpass filter 120 filters an intensity signal output from the second detector 116 based on the peaks of the power spectrum of the time-series signal. Computer 130 processes the signals output from detectors 115 and 116 and filtered by electronic bandpass filters 119 and 120.

Computer 130 includes an intensity ratio calculation unit 131, an oxygen saturation calculation unit 132, and a CPU 133. Computer 130 detects parameters (intensity, period, frequency) of a pulse wave signal from intensity fluctuations of the one light beam at the wavelength of 910 nm by using the output from second detector 116, and compares the intensity fluctuations of the one light beam at the wavelength of 910 nm to the a signal of the other light beam at the wavelength of 660 nm output from first detector 115. Oxygen saturation and other parameters are calculated from the intensities of the two light beams by the computer 130. Additionally, computer 130 calculates the blood flow rate from the intensity fluctuations of the one light beam at the wavelength of 910 nm by using the output from second detector 116. Then, oxygen metabolism is calculated from the oxygen saturation and the blood flow rate by computer 130. As previously mentioned, U.S. Pat. No. 8,082,015 describes certain techniques for calculating blood flow rate and oxygen metabolism. According to this patent, tissue metabolic rate of oxygen consumption ($TMRO_2$) may be calculated by combining the blood flow data and oxygen saturation data using an equation referred to as Fick's Law defined as $TMRO_2 = (OEF) \times (BF) \times ([O_2]_a)$, where $[O_2]_a$ is the arterial oxygen concentration, OEF is the oxygen extraction fraction defined as $([O_2]_a - [O_2]v)/([O_2]_a)$, and where subscripts "v" and "a" denote venous and arterial sides, and where BF is tissue blood flow. Then, assuming the arterial oxygen concentration, $[O_2]_a$, does not change (in steady-state), the relative change in oxygen metabolism can be shown to be: $rTMRO_2 = (rOEF) \times (rBF)$, where r denotes relative change, and where differential changes in the temporal decay of diffuse photon correlation functions yield rBF (a relative change in tissue blood flow).

<Detecting Pulse Wave Signal Using DWS>

DWS is an effective optical technique for studying the dynamics of scattered light. A diffusing wave spectroscopy (DWS) apparatus is more sensitive to optical scattering than to optical absorption. See, for example, Irwin et al., "Influence of tissue absorption and scattering on diffuse correlation spectroscopy blood flow measurements", Biomed. Opt. Exp., Vol. 2, No. 7, pp. 1969-1985, published 17 Jun. 2011 (herein referred as "NPL Reference 3"). In DWS, a laser light with a long coherent length is irradiated to a sample which is turbid media, in which the light is scattered multiple times. At least part of the scattered light is diffused through the sample and input into an optical detector via a pinhole or an optical fiber. The intensity of signal output from the optical detector fluctuates temporally. An autocorrelation function and its decay time are calculated from the fluctuating signal by using, for example, a correlator. The decay time of the autocorrelation function curve is related to the change in blood flow. In turn, as discussed above, the change in blood flow is related to the variations in light transmission through tissue which permits direct optical recording of the pulsatile component of arterial blood flow. Therefore, by combining the pulse oximeter which measures blood dynamics by calculating absorption ratios, and the DWS system which detects the pulse wave signal by calculating correlation parameters of arterial blood diffusion, oxygen saturation and other such parameters can be calculated with higher accuracy.

Still referring back to FIG. 2A, coherent light from the light sources 101 and 102 is guided by the SMF 104 to irradiate the sample 100. Scattered light that has diffused through the sample 100 is collected by the double-clad fiber 105 at a distance ρ away from the SMF 104. To detect the pulse wave signal using the DWS system, the light collected by DCF 105 is guided to the second detector 116 via lens 106, transmitted through the dichroic mirror 109, transmitted through the pinhole 110 and focused by the lens 107. Since the light beams which travel in the inner cladding of DCF 105 are blocked by the pinhole 110, the second detector 116 generates an electrical signal corresponding to the intensity of only the light traveling in the core of the fiber DCF 105. Therefore, the use of the DCF 105 as a common detection fiber for both the oximeter and DWS allows the detector 116 to detect a single speckle grain at a time. Then, correlator 117 (or computer 130) calculates an autocorrelation function $g2(\tau)$ from measurements of photon intensity output from detector 116.

As it is known to persons having ordinary skill in the art, the normalized (second-order) autocorrelation function $g2(\tau)$ for a transmission condition of scattered light through particles in turbid media is defined by Equation (1) using what is known as the "Siegert-relation". Equation (1) relates the second-order autocorrelation function $g2(\tau)$ with the first-order autocorrelation function $g1(\tau)$ as follows:

$$g_2(\tau) = 1 + \beta |g_1(\tau)|^2 \quad \text{Equation (1)}$$

where $$g_1(\tau) = \int_0^\infty P(s) e^{-(2\tau/t \frac{s}{l^*})} ds, \quad \text{Equation (1a)}$$

represents correlation for a monodisperse sample modeled as a semi-infinite thin slab.

In Equation (1), β (beta) is a coherence factor of the system; τ (tau) is the correlation time delay or correlation time constant. In Equation (1a), P is the probability or fraction of scattered intensity (fraction of photons) which travels a path length s through the sample (scattering medium); that is, s in Equation (1a) is the path length of a single photon passing through the sample after multiple scattering events. And $t=1/k_0^2 D$, where $k_o$ is a wave number (inverse of wavelength) of the light used to irradiate the sample, D is the particle diffusion coefficient, and l* is a mean free path length.

The mean free path length l* is the averaged distance between randomized scattering events in a suspension with very small particles. The mean free path length l* depends primarily on the number of target particles per unit volume, and on the effective cross sectional area for collision. The photon path length s is the total length of photon trajectory with N times scattering events in the medium (e.g., a suspension).

In practice, the signal output from the second detector 116 is transferred to correlator 117 for detection therein of an autocorrelation function and its decay time based on intensity fluctuations of the output signal. The correlator 117 can be implemented as a stand alone hardware correlator (as illustrated in FIG. 2A), or it can be a software-based correlator integrated within computer 130. The spectrum analyzer 118, as the name indicates analyses the spectrum of a signal, so it is able to obtain the power spectrum (signals in the frequency domain) of the signal produced by the correlator 117. Spectrum analyzers can obtain the spectrum of a signal in various ways. There are swept-tuned and Fast Fourier Transform (FFT) based spectrum analyzers. Similar to the correlator 117, the spectrum analyzer be implemented as a stand alone hardware device, or it can be a software-based spectrum analyzer integrated within computer 130. When the correlator and spectrum analyzer are software-based, the correlator 117 and spectrum analyzer 118 shown in FIG. 2A can be obviated.

In DWS, the optical intensity of light collected by a single mode fiber or collected by the core of double clad fiber is very week. Therefore, second detector 116 is implemented as a photon counting detector such as an avalanche photo diode (APD) or a photo multiplier tube (PMT) capable of detecting single photon events. That is, the above APD or PMT corresponding to at least detector 116 is preferably operated in Geiger-mode (as opposed to linear mode). In this case, the pulse signal is output from detector 116 according to arrival statistics of photons detected therein. The count of pulses per unit time in the pulse signal is proportional to the count of photons which are input to the detector in a given window of time. The autocorrelation function is then calculated using the time dependence of count of pulses.

The correlator 117 uses a distribution of arrival times of the pulses to quantify temporal fluctuations of the detected light intensity. As previously mentioned, the intensity autocorrelation function $g2(\tau)$ can be calculated by a dedicated hardware correlator, but it is also possible to compute the autocorrelation function using software correlators. See, for example, Wang et al., "Fast blood flow monitoring in deep tissues with real-time software correlators", BIOMEDICAL OPTICS EXPRESS, Vol. 7, No. 3, 1 Mar. 2016 (herein referred as "NPL Reference 4"), which is incorporated by reference herein in its entirety. Therefore, in the present embodiment, the calculation of autocorrelation function can be calculated by any of a hardware correlator, a software correlator module, or a combination of both.

The correlator 117 calculates the autocorrelation function $g2(\tau)$ from speckle intensity signals measured by the DWS system, as already explained above. In practice, the fluctuations of intensity signal output from detector 116 is used by correlator 117 (or computer 130) to calculate the autocorrelation function according to the following Equation (2):

$$g_2(\tau) = \frac{\langle I(0) I(\tau) \rangle}{\langle I \rangle^2} \qquad \text{Equation (2)}$$

In Equation (2), I(t) is the optical intensity signal obtained from detector 116 at time t, τ is the correlation time lag, and the angular brackets < > denote time averaging. From Equation (2), a time constant or decay time $\tau_c$ is calculated by fitting a function f(τ) to the correlation function according to Equation (2a):

$$f(\tau) = 1 + \beta \cdot \exp(-\tau/\tau_c) \qquad \text{Equation (2a),}$$

where β is the coherence factor.

For example, the curve fitting is performed using the least squares method. The residual sum of squares (RSS) is calculated using the following Equation (2b):

$$\text{RSS} = \Sigma_{i=1}^{n} (g2(\tau i) - f(\tau i)) \qquad \text{Equation (2b),}$$

where g2(τi) is the "i" measured intensity autocorrelation function. The coherence factor and decay time in Equation (2a) are optimized so that RSS is minimized.

<Calculation of Oxygen Saturation>

The time dependent signal of decay time is output from the correlator 117 and input to spectrum analyzer 118. Spectrum analyzer 118 performs Fourier analysis (fast Fourier transform) of the time dependent signal of decay time. Since the pulse wave is a repetitive time-series signal, the peak related to the period of the pulse wave can be identified from the spectrum calculated by Fourier analysis.

More specifically, turning now to FIGS. 10A through 10E, an explanation is given of the manner in which the pulse wave is used to perform more accurate calculation of oxygen saturation. As described above, in the hybrid oximeter/DWS system, the signal output by one of the detectors is used to obtain an autocorrelation function. In the embodiment of FIG. 2A, the output from the second detector 116 is used by the correlator 117. To that end, the signal output from detector 116 can be a digital output, as shown in FIG. 10A, or it can be an analog output as illustrated in FIG. 10B.

As illustrated in FIG. 10B, the output from detector 116 shows that the signal includes time-dependent intensity fluctuations. The intensity fluctuations are obtained as a result of light detection (photon counting) in real time. The intensity fluctuations may also be obtained when the photon count is averaged for predetermined periods of time. The detected variations of the photon count rate (or variations of the averaged photon count rate) reflect changes on the dynamics of hemoglobin within the measured volume (region) of the examined tissue sample. These intensity fluctuations are sampled at a predetermined rate (e.g., 10 μs/sample) for a desired period of time (50 ms) to generate a digital time-series signal.

An exemplary digital signal obtained by photon counting with an APD (detector 116) is illustrated in FIG. 10A. In FIG. 10A, it is shown that a detector designed to collect 100 thousand counts per second (100 kcps) and sampled at an average of once every 10 μs with a pulsewidth of about 10-20 nanoseconds (ns) will produce a time-series digital signal representative of the number of pulses occurring every 10 μs. Specifically, FIG. 10A exemplary shows that in each of a period from t1 to t2, and a period from t2 to t3 a single pulse is output from detector 116; and in a period from t3 to t4 two pulses are output from detector 116. However, in the period from t4 to t5 no signal is output from detector 116. The number of pulses output by detector 116 depends namely on the amount (number) of photons detected (counted) every given time window (10 μs). The mean number of pulses output by detector 116 depends on the mean intensity of light input to detector 116. In this case, the mean intensity of light is 100 kcps. It means that one pulse is output during 10 μs on an average.

The intensity fluctuations of the signal output from detector 116 are used to calculate an intensity correlation function, as that shown in FIG. 10C. FIG. 10C shows the autocorrelation function curve, which decays from its highest to its lowest value in a period of approximately 25 ms. The time decay $\tau_c$ depends on the blood flow amount, which in turn depends on the cardiac cycle, and accordingly a value of the time decay $\tau_c$ can be different for each cardiac cycle because the human cardiac cycle is not constantly uniform. In FIG. 10C, the intensity autocorrelation function represents a temporal autocorrelation function of the intensity fluctuations of detector 116 acquired using an integration time of approximately 25 ms at a sampling rate of 10 μs (10 μs/sample). The decay time $\tau_c$ is calculated by fitting the function f(τ) to the correlation function according to Equation (2a) described above. The time dependent signal of decay time $\tau_c$ is output from correlator 117 as a time-series signal, which is input to spectrum analyzer 118.

The spectrum analyzer 118 receives from correlator 117 a time-series signal of the decay time $\tau_c$ (a pulse wave) having the form illustrated in FIG. 10D. The spectrum analyzer 118 performs a Fourier Transform (FFT) process on the time-series signal shown in FIG. 10D. The result of the FFT process is a frequency-domain signal called the power spectrum. The spectrum analyzer 118 detects a peak (PR) of each pulsation from the power spectrum of the pulse wave signal, as shown in FIG. 10E. Then, the frequency (center frequency) of each peak of the power spectrum of the pulse wave signal is used to adjust the center frequency of the electronic bandpass filters 119 and 120.

The center frequency of filters 119 and 120 are adjusted based on the frequency of the peak signal extracted from the spectrum of the pulse wave signal. This pulse wave signal calculated by spectrum analyzer 118 is related to the time-varying pulse of arterial blood flow caused by the heartbeat. In this manner, the signals output from the first detector 115 and second detector 116 are adjusted (filtered or synchronized) by filters 119 and 120, respectively, even before any physiological parameters are calculated by computer 130. The variation in time of the signals output from band-pass filters 119 and 120 is caused only by the pulse detected by spectrum analyzer 118. Therefore, the signals output from (filtered by) band-pass filters 119 and 120 represent a true and effective peak intensity of the arterial blood flow. That is to say, any possible noise existing in the signals output from detectors 115-116 and received by filters 119-120 is removed, and only the intensity signals of the first and second wavelengths synchronized (or gated) with the pulse wave transmits through filters 119 and 120.

<Calculation of Physiological Parameters>

As previously noted, computer 130 calculates oxygen saturation from the intensities of the two signals output from detectors 115 and 116. The blood flow rate is calculated from the intensity fluctuation of the one light beam at the wavelength of 910 nm detected by one of the detectors. Oxygen metabolism can then be calculated from the oxygen saturation and the blood flow rate, in a known manner.

Oxygen saturation of hemoglobin is measured based on optical absorption ratios of absorbance of deoxyhemoglobin (Hb) and oxyhemoglobin (HbO$_2$). The absorbance OD($\lambda$) is calculated according to the Beer-Lambert law, defined by Equation (3), as follows:

$$OD(\lambda) = \log\left(\frac{I_0(\lambda)}{I(\lambda)}\right) =$$
$$\varepsilon_t(\lambda)c_t d_t + \varepsilon_v(\lambda)c_v d_v + [(\varepsilon_{Hb}(\lambda)c_{Hb} + \varepsilon_{HbO2}(\lambda)c_{HbO2})]d_a \quad \text{Equation (3)}$$

In Equation (3), $I_o(\lambda)$ is the intensity of light incident on the sample (tissue), $I(\lambda)$ is the intensity of light detected at the detector, $\lambda$ is the wavelength, $\varepsilon$ is absorption coefficient (cm$^{-1}$ L/mol), c is molar concentration (mol/L), and d is optical path length (cm). Since the absorption coefficient $\varepsilon$ depends on how the various absorbers interact with light within the sample, the first term on the right side of Equation 3 is the absorption in tissue; the second term is the absorption in the vein(s); and the third term is the absorption in the arteries. Here, it should be noted that Equation (3) does not include a term related to scattering; that is, diffusion principles are not taken into account in Equation (3) to calculate oxygen saturation.

According to Equation (3), it is assumed that the optical path length of light transmitted though arteries is pulsed by the heartbeat, and that the optical path lengths of general tissue and veins are not pulsed. In other words, it is conventionally assumed that the optical path length of artery absorption $d_a$ depends on time, and that the optical path lengths of tissue $d_t$ and veins $d_v$ do not depend on time. Therefore, Equation (3) generally consists of steady-state terms, and one time-dependent term. The time variation in the time-dependent term is the only term of absorption in arteries, which is the third term on the right side of Equation (3). Therefore, a pulse oximeter generally calculates oxygen saturation from the time variation term(s) in Equation (3). The time-dependent absorbance, $\Delta OD(\lambda)$ for wavelengths $\lambda_1$ and $\lambda_2$ of the two lights used in oximetry are given by the following Equations (4) and (5), as follows:

$$\Delta OD(\lambda_1) = [(\varepsilon_{Hb}(\lambda_1)c_{Hb} + \varepsilon_{HbO2}(\lambda_1)c_{HbO2})]\Delta d_a \quad \text{Equation (4)}$$

$$\Delta OD(\lambda_2) = [(\varepsilon_{Hb}(\lambda_2)c_{Hb} + \varepsilon_{HbO2}(\lambda_2)c_{HbO2})]\Delta d_a \quad \text{Equation (5)}$$

In Equations (4) and (5), $\Delta d_a$ is the time-dependent optical path length in the arteries. Therefore, arterial oxygen saturation (SpO$_2$) is calculated by using the following Equation (6):

$$SpO_2 = \frac{\varepsilon_{Hb}(\lambda_1)}{\varepsilon_{Hb}(\lambda_1) - \varepsilon_{HbO2}(\lambda_1)} + \frac{-\varepsilon_{Hb}(\lambda_2)}{\varepsilon_{Hb}(\lambda_1) - \varepsilon_{HbO2}(\lambda_1)} \frac{\Delta OD(\lambda_1)}{\Delta OD(\lambda_2)} \quad \text{Equation (6)}$$

Turning again, to FIG. 2A, the intensity ratio calculation unit 131 uses the filtered signals output from detectors 115 and 116 to calculate an intensity ratio thereof. To that end, the intensity ratio calculation unit 131 can first use the middle term of Equation (3) to calculate the natural logarithm ("log") of the intensity ratio of light at each wavelength. Then, the intensity ratio calculation unit 131 can use Equations (4) and (5) to calculate the time dependent absorbance at each wavelength. Finally, the oxygen saturation calculation unit 132 calculates oxygen saturation using Equation (6).

Here it should be noted that although the process for calculating the arterial oxygen saturation (SpO$_2$) disclosed herein may use the known Equations (3)-(6), this calculation is made more accurate than conventionally known processes because detection of the pulse wave signal has been improved by using the DWS system to more accurately detect peaks of the pulse wave and to filter, gate or synchronize the intensity signals of the pulse oximeter with the true peaks of the pulse wave signal.

<Control and Processing System>

Figure 3A:
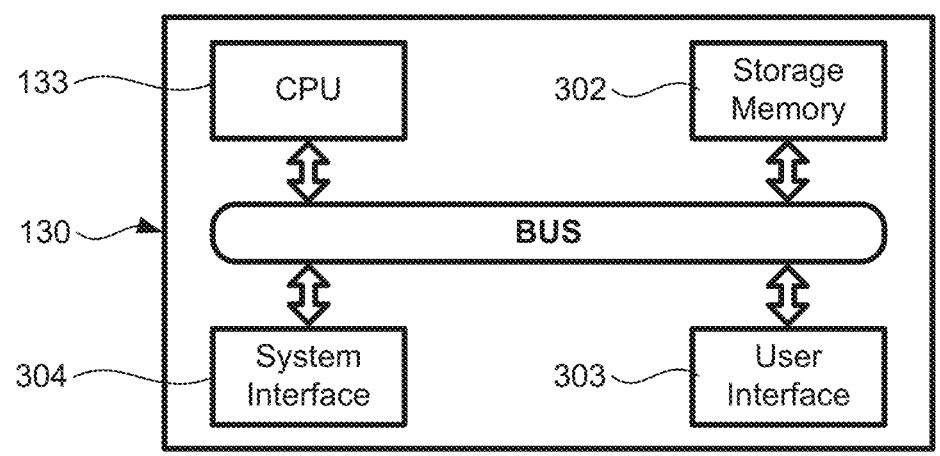
FIG. 3A a schematic block diagram of a control and processing system applicable to the various embodiments of a pulse oximeter and DWS hybrid system.

FIG. 3A is a schematic diagram of an exemplary computer control system for the combined oximeter and DWS system. As shown in FIG. 3A, the computer control system is representative of computer 130 shown in FIG. 2A. In FIG. 3A, the computer 130 includes central processing unit (CPU) 133, a storage memory (RAM) 302, a user input/output (I/O) interface 303, and a system interface 304.

The CPU 133 is comprised of one or more processors (microprocessors) configured to read and perform computer-executable instructions stored in the storage memory 302. The computer-executable instructions may include those for the performance of the novel processes, methods and/or calculations disclosed herein. For example, CPU 133 calculates speckle fluctuations of near-infrared diffuse light as temporal intensity fluctuations based on the light detected by the second detector 116 and filtered by electronic bandpass filter 120. In addition, CPU 133 calculates an intensity ratio, oxygen saturation value, blood flow value, oxygen metabolism value, and other parameters related thereto, as described more in detail elsewhere in this disclosure.

Storage memory 302 includes one or more computer-readable and/or writable media, and may include, for example, a magnetic disc (e.g., a hard disk drive HHD), an optical disc (e.g., a DVD®, a Blu-ray®, or the line), a magneto-optical disk, semiconductor memory (e.g., a non-volatile memory card, Flash® memory, a solid state drive, SRAM, DRAM), an EPROM, an EEPROM, etc. Storage memory 302 may store computer-readable data and/or computer-executable instructions including Operating System (OS) programs, and control and processing programs. The various components of the computer 130 communicate with each other via a data bus (BUS) in a known manner.

The user interface 303 provides a communication interface (electronic connections) to input/output (I/O) devices, which may include a keyboard, a display, a mouse, a printing device, a touch screen, a light pen, an external optical storage device, a scanner, a microphone, a camera, a drive, communication cable and a network (either wired or wireless). The system interface 304 also provides communication interfaces (electronic connections) for one or more of light sources 101-102, detectors 115-116, correlator 117, spectrum analyzer 118, and electronic bandpass filters 119-120. The detectors 115-116 may include an avalanche photodiode detector (APD), an array of APDs, a photomultiplier tube (PMT), a combination of the foregoing, or the like. Also, the function of the user interface 303 and of the system interface 304 may be realized by computer executable instructions (e.g., one or more programs) recorded on storage 302. Moreover, the computer 130 may comprise one or more additional devices, for example, components such as a communications or network interface, a circuit interface (e.g., a field-programmable gate array: FPGA) to control the one or more of the light sources 101-102, detectors 115-116, the correlator 117 and spectrum analyzer 118.

Figure 3B:
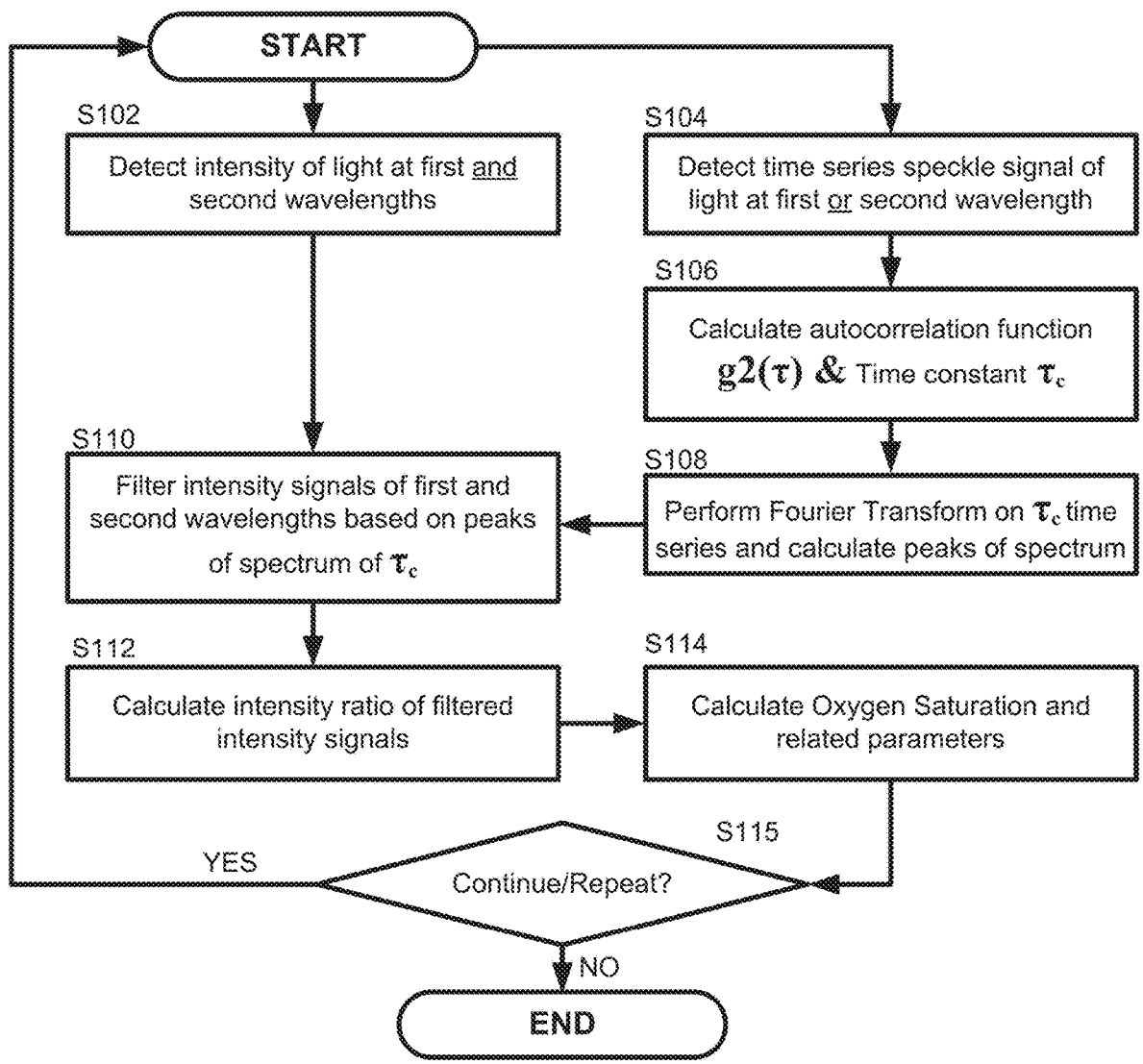
FIG. 3B illustrates an exemplary flow process for detecting the pulse wave signal and calculating oxygen saturation using the pulse oximeter and DWS hybrid system.

FIG. 3B illustrates an exemplary flow process for detecting the pulse wave signal and calculating oxygen saturation using the pulse oximeter and DWS hybrid system. In the process of FIG. 3B, the flow assumes that the oximeter and DWS system is in an operative state after an START signal. Therefore, in an operative state, at step S102, computer 130 controls light source 101 and 102 to irradiate sample 100 with light at first and second wavelengths. Upon irradiation, detectors 115 and 116 detect the intensities of light at the first and second wavelengths, as already described above. Simultaneously, at step S104, the detector 116 outputs a time series signal to correlator 117. At step S106, the correlator 117 uses the time series signal received from detector 116 to calculate an intensity autocorrelation function, and derives therefrom a time constant or time decay signal $\tau_c$. At step S108, the spectrum analyzer receives the time decay signal and performs Fourier transformation to obtain a frequency signal (a frequency spectrum) of the time decay signal. At step S110, computer 130 controls filters 119 and 120 to respectively filter the signals output from detectors 115 and 116. At step S110, to filter the intensity signals output for detectors 115 and 116, the center frequency of filters 119 and 120 is adjusted to match the frequency of peak of power spectrum of the time decay signal. At step S112, computer 130 uses the filtered signals to calculate the intensity ratio, and at step S114 computer 130 calculates the oxygen saturation and other parameters related to oxygen saturation. At steps S112 and S114, computer may use Equations (3)-(6). At step S115, an operator/user may be prompted whether to continue and repeat measurements, or to end the process.

Figure 4:
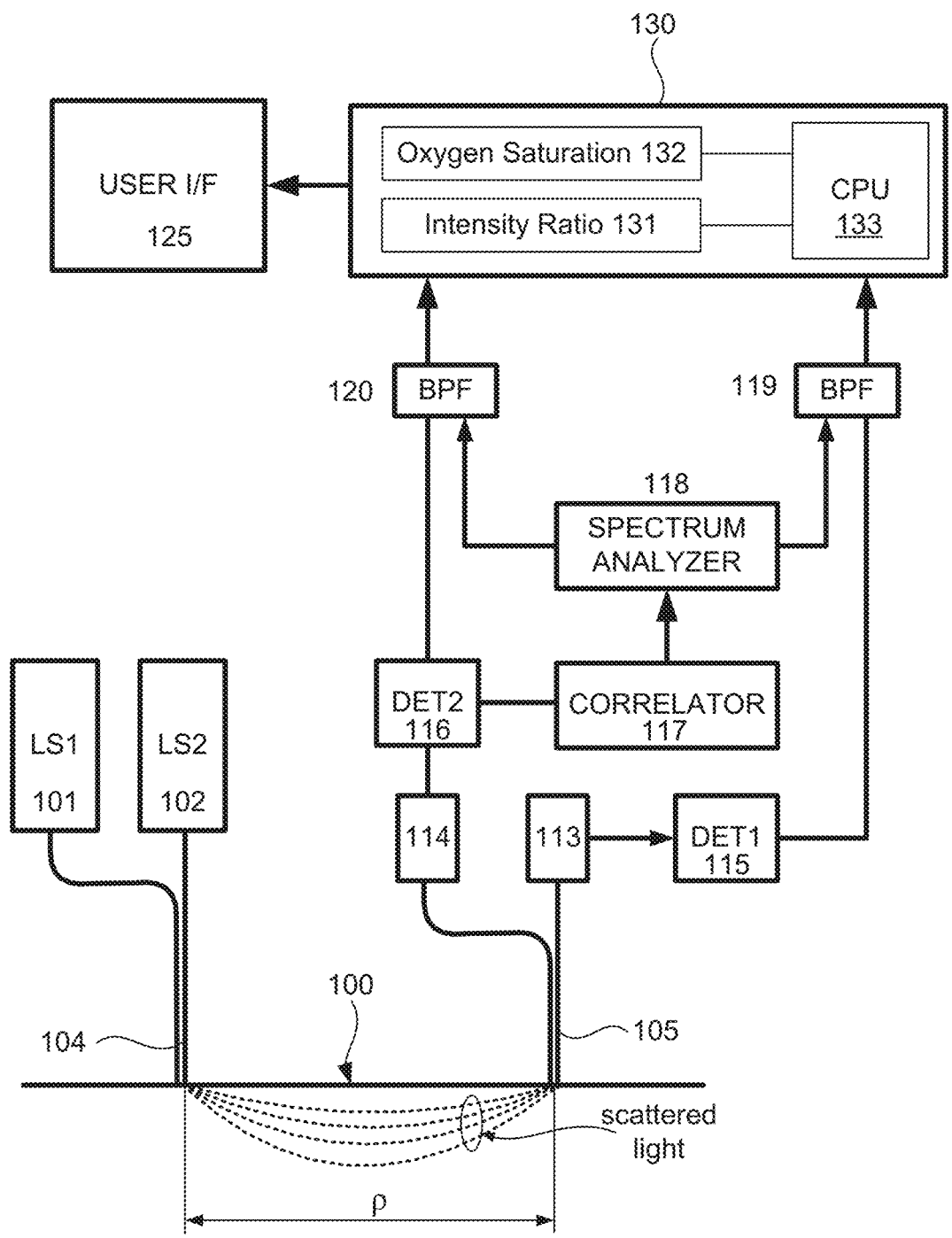
FIG. 4 illustrates a modification of the system shown in FIG. 2A.

FIG. 4 shows a first modification of the system described above. As shown in FIG. 4 the combined oximeter/DWS system is similar to that shown in FIG. 2A. FIG. 4 includes a first source-detector pair including the light source 101 and a detector 115, and a second source-detector pair including the light source 102 and a detector 116. In this first modification, the wavelength of light emitted from light source 101 is not limited to 660 nm; it is only preferable that it is shorter than Boo nm. The wavelength of light emitted from light source 102 is not limited to 940 nm; it is only preferable that it is longer than 800 nm. The coherence length of light emitted from at least one of the light sources 101 and 102 is longer than about 1 meter. The light beams emitted from light source 101 and from light source 102 are guided by independent fibers 104 and conveyed to sample 100, at a predetermined region of interest therein. In this disclosure, the fibers 104 are generally referred as a source fiber, but the number of fibers is not limited to single fiber. As described above with respect to FIG. 2A, one single mode fiber 104 can be used as the source fiber.

In the case of FIG. 4, two source fibers are shown; these fibers can be single-mode or few-modes fibers, alternatively, one source fiber can be used as in FIG. 2A. To deliver light more efficiently to the tissue sample 100, the distal end of the source fiber is in physical contact with the sample. However, it is also possible to irradiate the light into the sample 100 directly from the light sources 101 and 102 without the use of a source fiber. Within the sample 100, the light is scattered multiple times while it travels in a diffusive manner from the source fiber (fiber 104), and then the diffused light is collected by optical fibers 105. The optical fibers 105 can be collectively referred to as a detector fiber. In FIG. 4, the detector fiber includes two individual fibers connected to detectors 115 and 116, respectively. Of these two fibers, at least the fiber connected to detector 116 should be either single mode or few modes fiber. At least part of scattered light is collected by the one or more optical fibers 105 located a predetermined distance ($\rho$) away from the irradiation point. Again, as described above, a double-clad fiber can be used as the detector fiber 105, or individual fibers can be used. Moreover, it is also possible to collect scattered light without the use of optical fibers, by arranging the light sources 101 and 102 in direct contact with the sample. The light collected by the detector fiber(s) 105 is input to detectors 115 and 116 via optical filters 113 and 114, respectively. Filters 113 and 114 are optical bandpass filters each configured to transmit therethrough a light beam of a specific wavelength.

Notable differences between the system illustrated in FIG. 4 as compared to the system illustrated in FIG. 2A are that the system of FIG. 4 does not use a double-clad fiber as the detector fiber 105, and it does not use a dichroic mirror, a pinhole or optical lenses for collecting the scattered light. Instead, the system of FIG. 4 uses individual detector fibers 105 and individual optical filters 113 and 114. In FIG. 4, optical filter 113 is a bandpass filter that transmits a first wavelength and blocks a second wavelength, while optical filter 114 is a bandpass filter that transmits the second wavelength and blocks the first wavelength. The optical filters 113 and 114 are either integrated with the corresponding detectors 115 and 116, respectively, or the filters are connected to the respective detectors through the use of optical fiber connectors (e.g., ferrules).

In FIG. 4, the light emitted from light source 101 and collected by a first fiber 105 transmits through optical bandpass filter 113 and goes into the first detector 115. The light emitted from light source 102 and collected by a second detector fiber 105 transmits through optical bandpass filter 114 and goes into second detector 116. That is, the second detector 116 detects the light emitted by the second light source 102; the wavelength of light emitted by second light source 102 is longer than 800 nm. The signal output from second detector 116 is input to a correlator 117 in order to calculate the decay time of an autocorrelation function generated therein. A spectrum analyzer 118 measures the power spectrum of the autocorrelation function and its time decay, and detects peaks of the power spectrum of a time series signal output from the correlator 117. Filters 119 and 120 are electronic bandpass filters similar to those described in reference to FIG. 2A.

The center frequency of filters 119 and 120 is optimized based on the peaks of the power spectrum detected by spectrum analyzer 118. The electronic bandpass filter 119 filters an intensity signal output from the first detector 115; and the electronic bandpass filter 120 filters an intensity signal output from the second detector 116. A computer 130 calculates an intensity ratio of the light emitted by light source 101 and light source 102 and detected by detectors 115 and 116, respectively, by using the signals filtered by filters 119 and 120. Then, computer 130 calculates oxygen saturation and other parameters related thereto, based on the intensity ratio. Results of these and other measurements are output via a user interface 125, e.g., a liquid crystal display (LCD) or printer. Here, the process of calculating the intensity ratios uses Equations (3)-(5), and the process of calculating oxygen saturation uses Equation (6) in a manner similar to that described above in reference to FIG. 3B.

Figure 5:
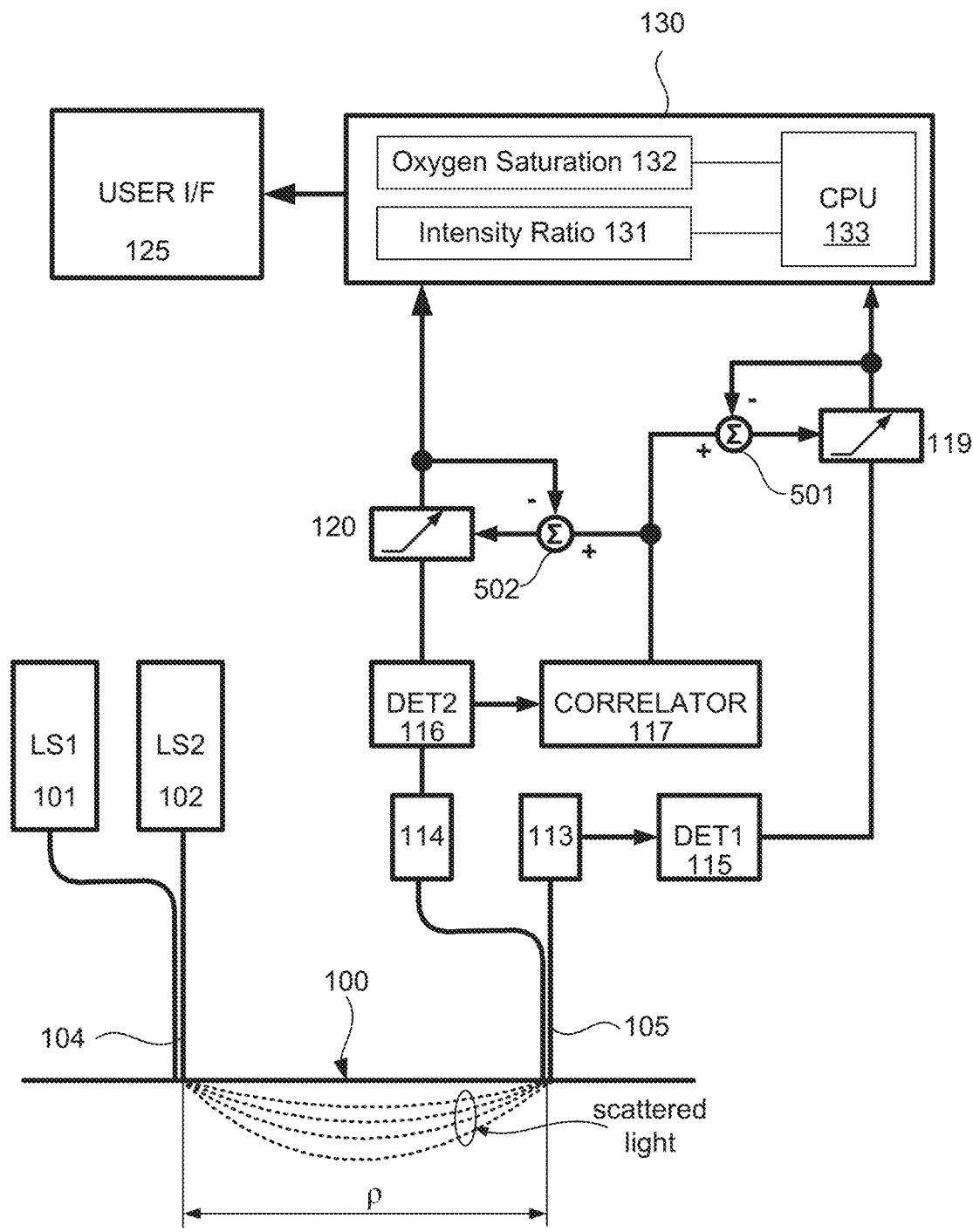
FIG. 5 illustrates another modification of the system shown in FIG. 2A.

FIG. 5 shows another modification of the system as described herein. In FIG. 5, filter 119 and filter 120 are each adaptive filters, where filter 119 includes a transfer function 501 and filter 120 includes a transfer function 502. The desired signal which is used in the adaptive filters is generated by correlator 117. Adaptive filters are often realized either as a set of program instructions running on an arithmetical processing device such as a microprocessor, or digital signal processing (DSP) chip, or as a set of logic operations implemented in a field-programmable gate array (FPGA) or in customized very-large-scale integrated (VLSI) circuits. Any of the above-known configurations can be adopted in the present application. Details about adaptive filters specifically applied to noise cancellation of electrocardiogram (ECG) signals can be found, for example, in "Adaptive noise cancelling: principles and applications", by Widrow et al., Proc. IEEE, 63(12), 1692-1716, December 1975 (herein "NPL Reference 5").

In FIG. 5, adaptive filter 119 receives the intensity signal output by detector 115, and adaptive filter 120 receives the intensity signal output by detector 116. That is, the intensity signal output by detector 115 is an input signal $x1(n)$ for adaptive filter 119, and the intensity signal output by detector 116 is an input signal $x2(n)$ for adaptive filter 120. Filter 119 computes an output signal $y1(n)$ based on its transfer function, and filter 120 computes an output signal $y2(n)$ based on its transfer function. Correlator 117 outputs a time-series signal which is the time dependent decay time of the autocorrelation function. The output of each adaptive filter is compared to the signal received from the correlator 117 (the desired response signal d(n)).

The error e(n) output by the transfer function of each adaptive filter is the difference between the desired signal and the output signal, such that $e1(n)=d1(n)-y1(n)$ and $e2(n)=d2(n)-y2(n)$. The adaptive filter is adjusted so that the error e(n) of the output signal is iteratively minimized and/or eliminated. To that end, the error signal is fed back into the filter transfer function which iteratively alters (adapts) the parameters of the filter from a time n to a time (n+1), as it is well known to those skilled in the art. The transfer functions 501 and 502 of the adaptive filters 119 and 120, respectively, are optimized so that a difference (error) between the signal output from the correlator 117 (desired signal) and the signal output from the adaptive filter is iteratively minimized. In this manner, the signals output from the optical detectors 115 and 116 are filtered (adjusted) by the adaptive filters 119 and 120 using the time-series signal output from the correlator 117. Then, computer 130 calculates the absorption ratio, and the oxygen saturation parameters using the filtered signals in the manner already described above in reference to FIG. 3B. An advantage of using adaptive filters, as compared to fixed filters (bandpass filters), is that adaptive filters have the ability to adjust their own parameters automatically, and the design of such adaptive filters requires minimum or no a priori knowledge of the input signal or noise characteristics; it is only required to have an accurate reference (or desired) signal to which the output of the filter must be compared.

Figure 6:
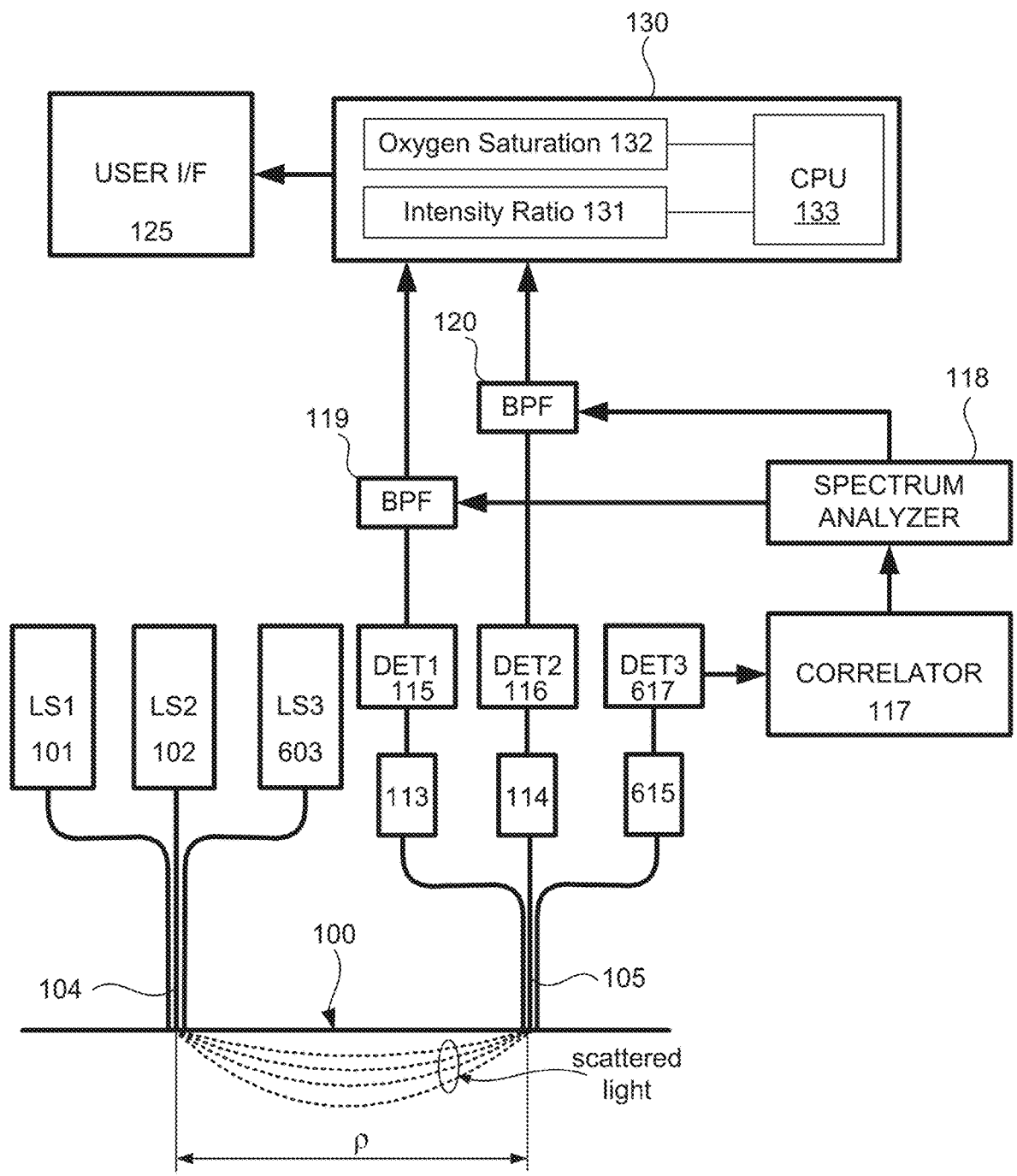
FIG. 6 illustrates a hybrid system combining a pulse oximeter and DWS apparatus.

FIG. 6 illustrates other embodiments of a hybrid system combining a pulse oximeter and DWS apparatus. In these embodiment, the system includes three source-detector pairs including a first source-detector pair formed by a first light source 101 and a first detector 115, a second source-detector pair formed by a second light source 102 and a second detector 116, and a third source-detector pair formed by a third light source 603 (LS3) and a third detector 617 (DET3). Similar to the discussion for FIG. 2A above and modifications thereof, light sources 101, 102 and 603 can be implemented as individual semiconductor laser sources or individual LED sources each generating the desired wavelength. The photodetectors 115, 116 and 617 may be implemented as individual avalanche photodiodes (APDs), as separated arrays of APDs, as PMTs, or similar photon counting photodetectors.

The wavelength of light source 101 is shorter than 800 nm. The wavelength of the second light source 102 is longer than 800 nm. The wavelength of third light source 603 is located at around 800 nm. The light output from the light sources 101, 102 and 603 is irradiated to the sample via optical fibers 104. FIG. 6 shows one fiber 104 for each light source, but a single fiber may be connected by one or more fiber couplers to the three light sources. Fiber 104 is collectively referred to as a source fiber. In FIG. 6, the source fiber includes one single mode fiber 104 for each of the three light sources. The distal end of the fibers 104 are placed in physical contact with sample 100. The light from light sources 101, 102 and 603 can instead be irradiated onto the sample 100 without the use of source fibers. The light of the various wavelengths, after undergoing multiple scattering in the sample 100, is collected by optical fibers 105 which are collective referred to as a detector fiber. In FIG. 6, at least the fiber connected to detector 617 is a single mode or few-modes fiber. The fibers connected to detectors 115 and 116 are individual single mode fibers, individual few modes fibers, a multi mode fiber, or combinations thereof. It is also possible to collect the scattered light using conventional optics, such as a prism, a waveguide or lenses, instead of optical fibers.

The light output from first light source 101 (wavelength lower than 800 nm) is input to first detector 115 via an optical bandpass filter 113. The light output from the second light source 102 (wavelength higher than 800 nm) is input to the second detector 116 via an optical bandpass filter 114. The light output from the third light source 603 (wavelength centered on 800 nm) is input to the third detector 617 via an optical bandpass filter 615.

The signal output from the third detector 617 is a pulse wave signal to be processed by the correlator 117 and analyzed by spectrum analyzer 118 to accurately detect the pulse wave parameters based on light diffusion principles. To that end, the signal output from the third detector 617 is input to correlator 117 in order to calculate decay times of a time-series intensity autocorrelation function. The signal which is output from correlator 117, and the time dependent decay times are input to spectrum analyzer 118. Spectrum analyzer 118 performs Fourier transform processing on the time-series signal, calculates a power spectrum the decay time function (signal), and detects peaks thereof.

Filter 119 and filter 120 are electrical bandpass filters. The center frequencies of filter 119 and filter 120 are changed based on the center frequency of the peak of the spectrum detected by spectrum analyzer 118. The signals output from the first detector 115 and the second detector 116 are filtered by filter 119 and filter 120, respectively. The intensity ratio calculation unit 131 in computer 130 calculates the intensity ratio by using the signals filtered by filter 119 and filter 120. Then, the oxygen saturation calculation unit 132 calculates the oxygen saturation using the intensity ratio. Results are output via a user interface 125, such as a liquid crystal display (LCD) or printer.

By distinguishing the light for DWS from the lights for pulse oximeter, the wavelength of light for DWS is optimized independently. In general, the scattering coefficient of tissue is reduced by increasing wavelength because of Rayleigh and Mie scatterings. The detected light intensity depends on depth of tissue of interest and scattering characteristics. By changing the wavelength of light for DWS, the detected light intensity can be optimized. Although the wavelengths of 660 and 910 nm are appropriate for a pulse oximeter, they may not be appropriate for DWS because the absorption and scattering coefficients at 660 nm may be too large and the scattering coefficient at 910 nm may be too low. Therefore, according to these embodiments, it is advantageous to detect the pulse wave with the DWS apparatus at a wavelength which is centered approximately at an isosbestic point (i.e., a wavelength near 800 nm where the total absorbance of the tissue sample is substantially unchanged and the blood flow is independent of oxygenation). That is, by monitoring fluctuations in the intensity of light that diffuses through the tissue, it possible to more effectively measure the pulse rate independent of oxygenation.

Figure 7:
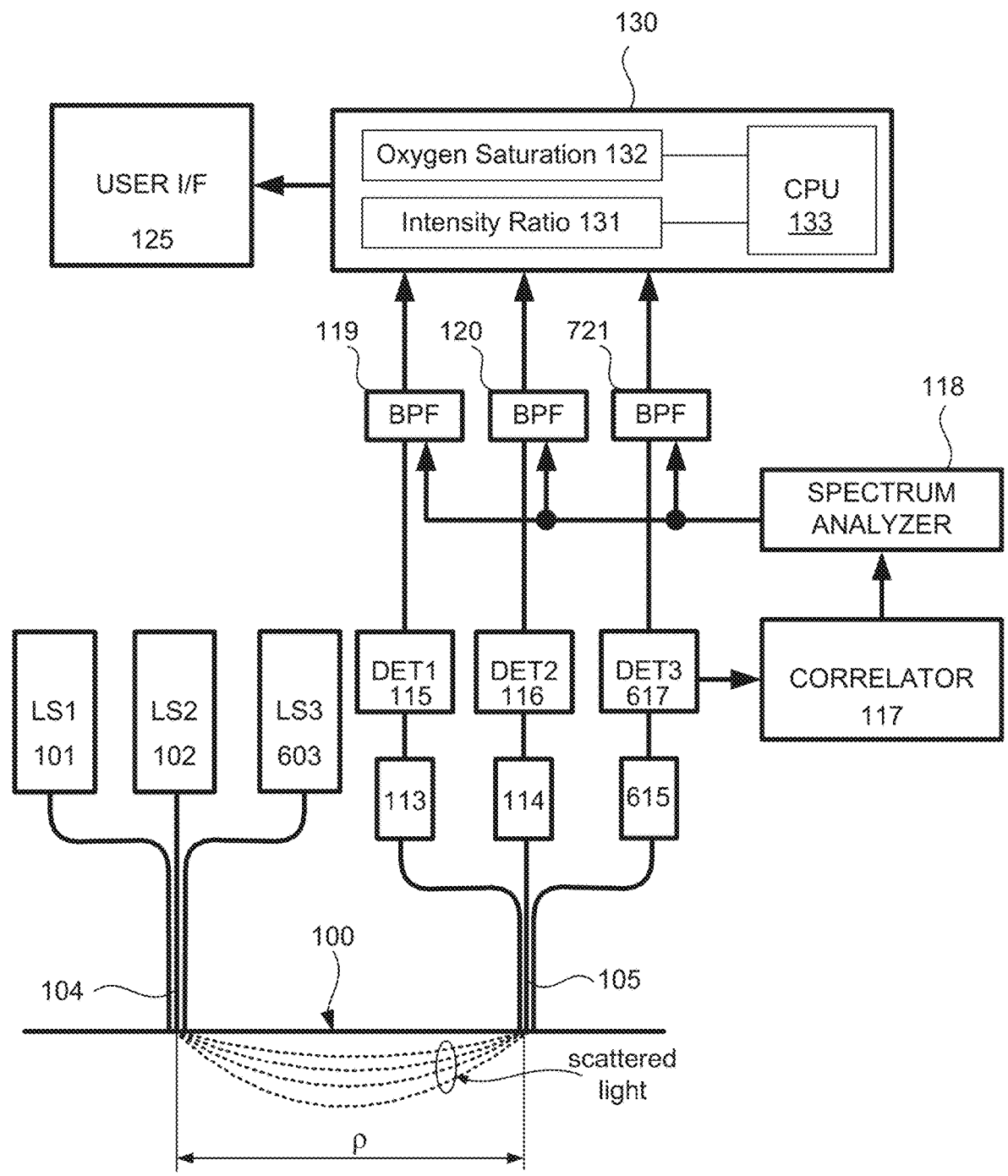
FIG. 7 illustrates a first modification of the system shown in FIG. 6.

FIG. 7 illustrates a first modification of the system shown in FIG. 6. Similar to the system of FIG. 6, the shown in FIG. 7 includes three source-detector pairs. A first source-detector pair is formed by a first light source 101 and a first detector 115; a second source-detector pair is formed by a second light source 102 and a second detector 116; and a third source-detector pair is formed by a third light source 603 and a third detector 617.

The wavelength of first light source 101 is shorter than 800 nm. The wavelength of second light source 102 is longer than 800 nm. The wavelength of third light source 603 is centered at around 800 nm. The light output from light sources 101, 102 and 603 is irradiated to the sample 100 via individual optical fibers 104 collectively referred to as source fiber. The light is scattered multiple times while it is diffusively transmitted through sample 100, and the scattered light is collected by optical fibers 105 collectively referred to as detector fiber.

The light output form first light source 101 and transmitted through the sample (tissue) is input to first detector 115 via an optical bandpass filter 113. The light output from second light source 102 and transmitted through the sample is input to second detector 116 via an optical bandpass filter 114. The light output from third light source 603 and transmitted through the sample is input to third detector 617 via an optical bandpass filter 615. The signal output form third detector 617 is input to correlator 117 in order to calculate the decay time of intensity autocorrelation functions. The signal which is output from correlator 117 and the time-dependent decay time signal (function) is input to spectrum analyzer 118 which performs Fourier transform processing, measures a power spectrum and detects peaks of the power spectrum. Filter 119, filter 120, and filter 721 are electronic bandpass filters. The center frequencies of filter 119, filter 120 and filter 721 are changed based on a center frequency of the peak detected by spectrum analyzer 118. The signals output from detector 115, detector 116, and detector 617 are respectively filtered by filter 119, filter 120 and filter 721. The computer 130 then calculates intensity ratios and oxygen saturation parameters using the filtered three signals.

An example of a pulse oximeter which employs three or more signals at different wavelengths is described in U.S. Pat. No. 3,638,640. In order to measure oxygen saturation, at least two signals at different wavelengths are needed. Another signal at a different wavelength from the above wavelengths is added as a reference signal. An advantage of using three wavelengths is to cancel a perturbation which affects to all signals by using the reference signal. A disadvantage, however, is that it is not possible to remove the perturbation which affects to only a part of signals (e.g., to only one signal).

In contrast, by distinguishing the light for DWS from the lights for pulse oximeter, the signal corresponding to the wavelength of light for DWS is optimized independently. Then, by filtering all three signals output from detector 115, detector 116 and detector 617 according to the center frequency of the peak spectrum of the DWS signal (pulse wave signal), the detected light intensity can be optimized.

Figure 8A:
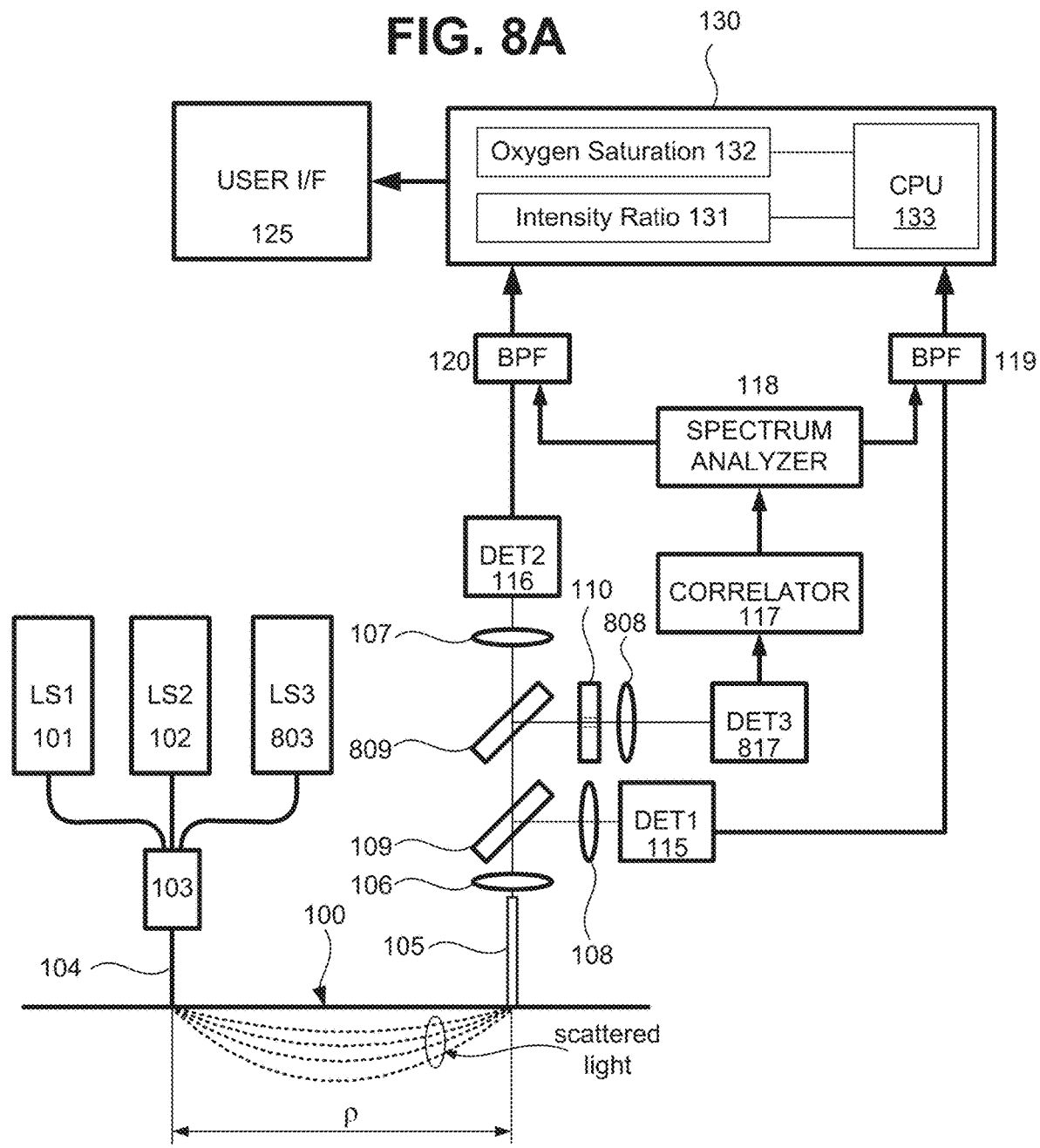
FIG. 8A illustrates another modification of the system shown in FIG. 6.

FIG. 8A illustrates another modification of the system shown in FIG. 6. Similar to the system of FIG. 6, the system shown in FIG. 8A includes three source-detector pairs. A first source-detector pair is formed by a first light source 101 and a first detector 115; a second source-detector pair is formed by a second light source 102 and a second detector 116; and a third source-detector pair is formed by a third light source 803 and a third detector 817.

The wavelengths of the light sources 101, 102 and 803 are, for example, 660, 910 and 780 nm, respectively. The light beams which are output from the three light sources are combined by a wavelength combiner 103 (e.g., one or more fiber couplers). The three light beams of the three different wavelengths are carried to sample 100 by one single mode fiber 104. As shown in FIG. 8A, the distal end of SMF 104 is preferably in physical contact with the tissue sample 100, and the proximal end of the SMF 104 is connected to the light sources 101, 102 and 803 via the wavelength combiner (fiber coupler) 103 and respective single mode fibers. The combined light beams irradiated to the sample 100 are scattered multiple times within the sample. At least part of the scattered light is collected by a double-clad fiber (DCF) 105 at a distance (ρ) away from the illumination point. The structure of the DCF used in this embodiment is similar to that shown in FIG. 2B.

Figure 8B:
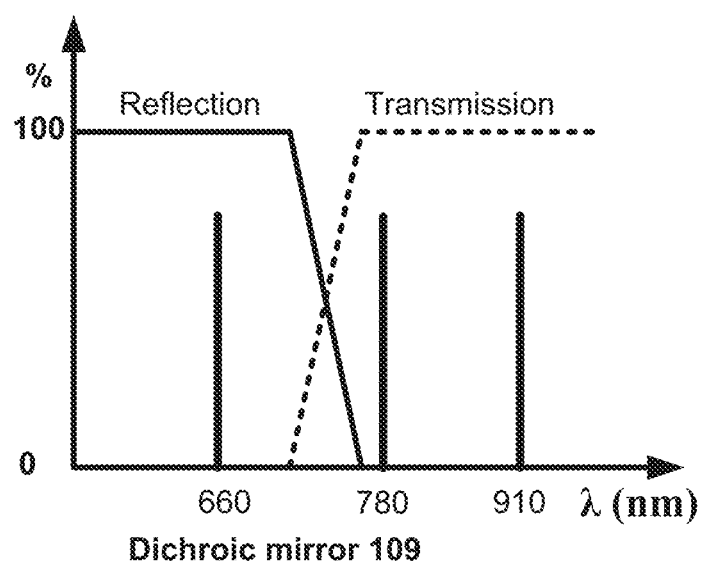
FIG. 8B illustrates transmission and reflection characteristics of a first dichroic mirror.
Figure 8C:
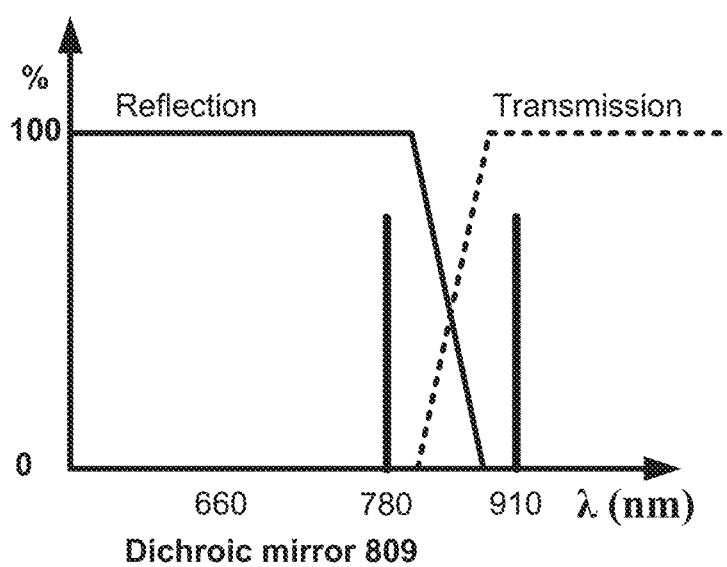
FIG. 8C illustrates transmission and reflection characteristics of a second dichroic mirror used in the system of FIG. 8A.

The collected light beams of light at wavelengths 660 nm, 780 nm and 910 nm propagate in both the core and the inner cladding of the DCF 105. A collimating lens 106 is used at the proximal end of DCF 105 to guide the collected light to the detectors. The light beam at the wavelength of 660 nm transmitted through the sample and collected by DCF 105 is reflected by a first dichroic mirror 109 and input to the first detector 115 via a lens 108. The light beams at the wavelengths of 780 nm and 910 nm are transmitted through the first dichroic mirror 109. The light beam at the wavelength of 910 nm transmits through a second dichroic mirror 809 and is input to a second detector 116 via a lens 107. On the other hand, the light beam at the wavelength of 780 nm is reflected by the second dichroic mirror 809 and is input to a third detector 817 via a pinhole 110 and a focusing lens 808. FIG. 8B illustrates transmission and reflection characteristics of the first dichroic mirror 109, and FIG. 8C illustrates transmission and reflection characteristics of the dichroic mirror 809 used in the system of FIG. 8A.

As a result, at the wavelengths of 660 nm and 910 nm, the light beams which propagate in both the core and the inner cladding of DCF 105 are respectively input to the detectors 115 and 116 without being affected by the light at 780 nm wavelength. At the wavelength of 780 nm, the light beam which propagates in the core of DCF 105 is input to the detector 817 and the light which propagates in the inner cladding of DCF 105 is blocked from reaching detector 817 by the pinhole 110. Therefore the detector 817 can effectively detect only light at 780 nm to more accurately quantify the diffusion effects of the tissue sample 100.

The signal output from the third detector 817 is the pulse wave signal to be analyzed to accurately detect the pulse wave parameters based on light diffusion principles. The signal output from the third detector 817 is input to correlator 117 in order to calculate decay times of a time-series intensity autocorrelation function. The signal which is output from correlator 117, and the time dependent decay time are input to spectrum analyzer 118. Spectrum analyzer 118 calculates a power spectrum and detects peaks thereof. The intensity ratio calculation unit 131 in computer 130 calculates the intensity ratio by using the signals filtered by bandpass filter 119 and bandpass filter 120. Then, the oxygen saturation calculation unit 132 calculates the oxygen saturation is using the intensity ratio, as describe above in reference to FIG. 3B. As discussed above, it is considered advantageous to detect the pulse wave with the DWS apparatus at wavelength which is centered approximately at an isosbestic point (i.e., a wavelength at which the total absorbance of the tissue sample is substantially unchanged).

EXEMPLARY APPLICATIONS

The monitoring of oxygen saturation with pulse oximeters can be performed in several locations of the human body. Transmission pulse oximeters are usually shaped as clamping probes that can be attached to earlobes, fingertips, and toes (an anatomical extremity) of patients. Reflection pulse oximeters are built as flexible or rigid bands to be applied to the forehead, temples, or other body surfaces (leg or arm) of patient convenient for detecting light reflected (backscattered) from patient.

Figure 9A:
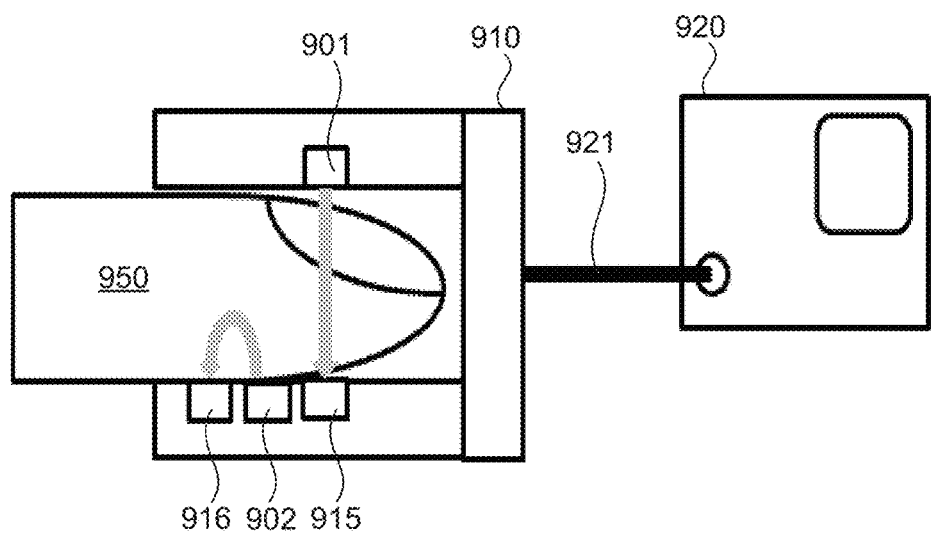
FIGS. 9A, 9B and 9C illustrate examples of the combined (hybrid) pulse oximeter/DWS system.

One of the most common applications for a pulse oximeter apparatus is the finger pulse oximeter. FIG. 9A shows an example of the combined (hybrid) pulse oximeter/DWS system where a clamping probe 910 is applied to a patient's finger 950. In general, a transmissive finger-type pulse oximeter is used where the light sources and the detectors are located so that the light transmits through the finger. However, it is also possible to realize a reflection-type finger pulse oximeter. Moreover, when using the hybrid system disclosed herein, it is possible to realize a hybrid system where a transmissive oximeter and a reflection-type DWS are combined. FIG. 9A is an example of one such combined pulse oximeter and DWS system of a finger-type probe 910 connected to a console 920. In FIG. 9A, a first source-detector pair including a light sources 901 and detectors 915 is used to measure absorption based on light of a first and second wavelengths transmitted through the finger 950, and a second source-detector pair including a light source 902 and a detector 916 is used to measure absorption based on light of a third wavelength reflected (backscattered) from the finger 950. In addition, the third source-detector pair 902-916 is used to measure a pulse wave signal based on the light of second wavelength reflected (backscattered) from the finger 950. The probe 910 is optically and/or electronically connected to a console 920 through wired or wireless connections 921.

Figure 9B:
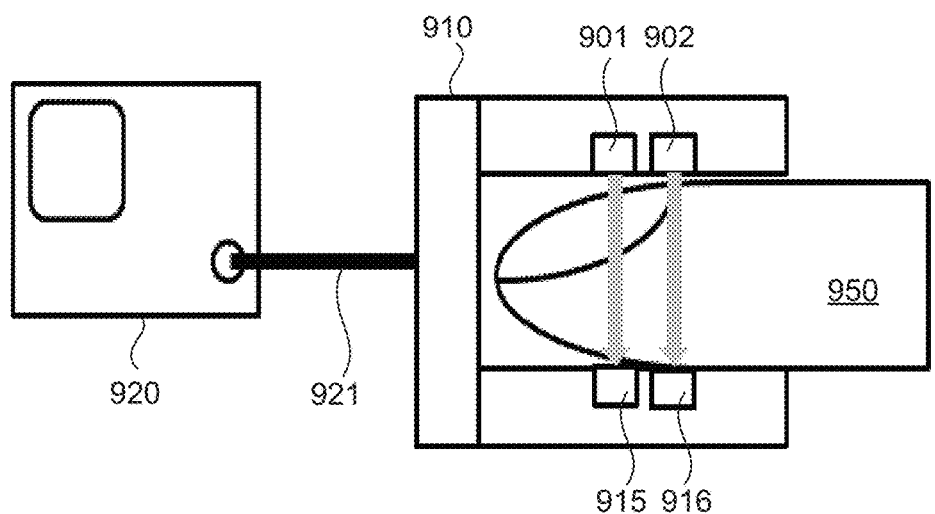

FIG. 9B shows an additional example of the combined (hybrid) pulse oximeter/DWS system. In FIG. 9B, the finger-type clamping probe 910 is similar to that of FIG. 9A except for the arrangement of the light sources 901-902 and detectors 915-916. Specifically, FIG. 9B shows the combined pulse oximeter and DWS system where a first source-detector pair 901-915 and a second source-detector pair 902-916 are used to the measure absorption ratios and the pulse wave signal based on light of first and second wavelengths transmitted through the finger 950. The probe 910 is optically and/or electronically connected to the console 920 via connection 921.

Figure 9C:
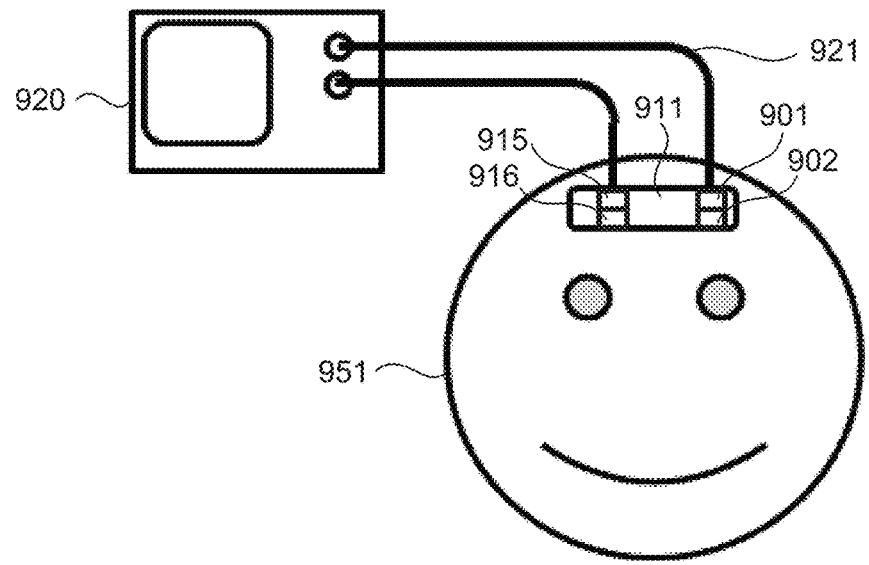

FIG. 9C shows another non-limiting example of the combined (hybrid) pulse oximeter/DWS system. In FIG. 9C, a band-shaped probe 911 is attached to the forehead of a subject 951. The probe 911 includes first and second light sources 901-902 and first and second detectors 915 and 916 similar to those shown in FIGS. 9A and 9C. However, in FIG. 9C, optical absorption ratios and pulse wave measurement are based on reflection (backscattering) of light of first and second wavelengths.

While the present patent application has been described with reference to exemplary embodiments, it is to be understood that the invention is not limited to the disclosed exemplary embodiments. For example, various numbers of sources and detectors and thus source-detector pairs and distances thereof may be used within the scope of the present disclosure. In some embodiments, there are two or more source-detector pairs and the distances thereof may be substantially the same distance for each pair, within a reasonable tolerance. In the various embodiments, it is contemplated that, to efficiently deliver and collect light to/from the subject, the distal ends of the source and detector fibers are placed in physical contact with the tissue of the subject. To that end, optical matching materials (e.g., gel) may be used between the distal end of the fibers and the tissue, as necessary. Alternatively, light can be delivered to and collected from the subject using other conventional optical elements such as waveguides, lenses, prisms and the like, without the use of optical fibers. In that case, each of such conventional optical elements may transmit (or collect) a single or multiple wavelengths of light. For example, in FIG. 9c, the typical source-detector distance is from 20 to 30 mm, which depends on the depth of interest.

Therefore, the scope of the following claims is to be accorded the broadest interpretation so as to encompass all possible modifications and equivalent structures and functions. To that end, it must be noted that the terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification and claims, specify the presence of stated features, integers, steps, operations, elements, and/or components, but do not preclude the presence or addition of one or more other features, integers, steps, operations, elements, components, and/or groups thereof not explicitly stated.

Reference 1: "Signal Extraction Technology", Technical Bulletin 1, Masimo Corporation, 2006

Reference 2: T. Duran et al., "Does the photon-diffusion coefficient depend on absorption?", J. Opt. Soc. Am. A/Vol. 14, No. 12/December 1997

Reference 3: Irwin et al., "Influence of tissue absorption and scattering on diffuse correlation spectroscopy blood flow measurements", Biomed. Opt. Exp., Vol. 2, No. 7, pp. 1969-1985, published 17 Jun. 2011

Reference 4: Wang et al., "Fast blood flow monitoring in deep tissues with real-time software correlators", BIOMEDICAL OPTICS EXPRESS, Vol. 7, No. 3, 1 Mar. 2016.

Reference 5: Widrow et al., "Adaptive noise cancelling: principles and applications", Proc. IEEE, 63(12), 1692-1716, December 1975.

What is claimed is:

1. An integrated device for analyzing tissue, comprising:
   two or more light sources configured to irradiate a tissue sample with a light of first wavelength and a light of second wavelength different from the first wavelength;
   two or more detectors configured to detect an intensity of the light of first wavelength and an intensity of the light of second wavelength transmitted through the tissue sample;
   a correlator configured to calculate an intensity autocorrelation function and a decay time of the autocorrelation function based on temporal intensity fluctuations of one of the light of first wavelength and the light of second wavelength transmitted through the tissue sample, wherein the correlator generates a time-series signal of the decay time of the intensity autocorrelation function;

a spectrum analyzer configured to obtain a power spectrum of the time-series signal and to detect peaks of the power spectrum; and a processor configured to quantify the intensity of the light of first wavelength and the intensity of the light of second wavelength transmitted through the tissue sample and detected by the two or more detectors, and quantify the temporal intensity fluctuations in the one of the light of first wavelength and the light of second wavelength transmitted through the tissue sample, wherein the processor synchronizes the intensity of the light of first wavelength and the intensity of the light of second wavelength based on the peaks of the power spectrum which correspond to peak intensities of the temporal intensity fluctuations of the one of the light of first wavelength and the light of second wavelength, and wherein, based on the synchronized intensity of the light of first wavelength and intensity of the light of second wavelength, the processor is configured to calculate one or more of an oxygen saturation value, and a blood flow value within the tissue sample.

2. The integrated device according to claim 1, further comprising:

two or more electronic bandpass filters operatively coupled to the spectrum analyzer and the two or more detectors, wherein center frequencies of the two or more electronic bandpass filters are changed based on a center frequency of the peaks of the power spectrum, wherein two or more electric signals output from the two or more detectors are respectively filtered by the two or more electronic bandpass filters, and wherein the processor calculates the one or more of an oxygen saturation value, a blood flow value, and oxygen metabolism within the tissue sample by using the two or more electric signals filtered by the two or more electronic bandpass filters.

3. The integrated device according to claim 1, further comprising:

two or more adaptive filters operatively coupled to the spectrum analyzer and the two or more detectors, wherein signals output from the two or more detectors are respectively input into the two or more adaptive filters, and the time-series signal output from the correlator is used a reference signal for each of the two or more adaptive filters, wherein transfer functions of the two or more adaptive filters are adaptively adjusted such that a difference between the time-series signal output from the correlator and a signal output from each adaptive filter is minimized, wherein the processor calculates the one or more of an oxygen saturation value, a blood flow value, and oxygen metabolism value within the tissue sample using the signals output from the two or more adaptive filters.

4. The integrated device according to claim 1, further comprising:

a light delivering optical system in optical communication with the two or more light sources for irradiating the tissue sample with the light of first wavelength and the light of second wavelength, the light delivering optical system including an optical fiber selected from a single mode fiber, a few-modes fiber, and a multi-modes fiber having a distal end thereof in physical contact with the tissue sample, and a proximal end thereof connected to the two or more light sources via a coupler.

5. The integrated device according to claim 4, further comprising:

a light collecting optical system for collecting the light of first wavelength and the light of second wavelength transmitted through the tissue sample, the light collecting optical system including a double clad fiber having a distal end thereof in physical contact with the tissue sample and a proximal end thereof in optical connection with the two or more detectors, wherein the double clad fiber includes a core, an inner cladding surrounding the core, and an outer cladding surrounding the inner cladding, and wherein, of the collected light, the light of first wavelength and the light of second wavelength are transmitted through both the core and the inner cladding of the double clad fiber.

6. The integrated device according to claim 5, further comprising:

an optical filter for selectively dividing the light of first wavelength from the light of second wavelength transmitted through the double clad fiber; and a spatial filter for dividing the collected light which propagates in the core from the collected light which propagates in the inner cladding of the double clad fiber.

7. The integrated device according to claim 1, wherein the two or more light sources include a first light source configured to emit light of the first wavelength in a range between 600 nm to 800 nm, and a second light source configured to emit light of the second wavelength in a range between 800 nm to 1000 nm, and wherein a coherence length of the second light source at the second wavelength is equal to or longer than a coherence length of the first light source at the first wavelength.

8. The integrated device according to claim 1, wherein the two or more light sources include two or more of laser diodes, solid-state lasers, fiber lasers, or light emitting diodes.

9. The integrated device according to claim 1, wherein the two or more detectors include two or more of an avalanche photodiode, an array of avalanche photodiodes, and a photomultiplier tube.

10. The integrated device according to claim 1, wherein the two or more light sources include a first light source configured to emit light of the first wavelength in a range between 600 nm to 800 nm, a second light source configured to emit light of the second wavelength in a range between 800 nm to 1000 nm, and a third light source configured to emit a light of third wavelength which is an isosbestic wavelength of the tissue sample.

11. The integrated device according to claim 1, further comprising:

a first double clad fiber for delivering light from the two or more light sources to the tissue sample, wherein the light of first wavelength output from a first light source propagates in the core of the first double clad fiber, and the light of second wavelength output from a second light source propagates in the inner cladding of the first double clad fiber;

a second double clad fiber for collecting from the tissue sample light of the first wavelength and light of the second wavelength transmitted through the tissue sample,
   wherein the second double clad fiber includes a core, an inner cladding surrounding the core, and an outer cladding surrounding the inner cladding, and
   wherein, of the collected light, the light of first wavelength and the light of second wavelength are transmitted through both the core and the inner cladding of the double clad fiber.

12. The integrated device according to claim 11, further comprising:
   an optical filter for selectively dividing the light of first wavelength from the light of second wavelength transmitted through the second double clad fiber; and
   a spatial filter for dividing the collected light which propagates in the core from the collected light which propagates in the inner cladding of the second double clad fiber.

13. A method for analyzing tissue with an integrated device, comprising:
   irradiating a tissue sample with two or more light sources emitting a light of first wavelength and a light of second wavelength different from the first wavelength;
   detecting, with two or more detectors, an intensity of the light of first wavelength and an intensity of the light of second wavelength transmitted through the tissue sample;
   calculating an intensity autocorrelation function and a decay time of the autocorrelation function based on temporal intensity fluctuations of one of the light of first wavelength and the light of second wavelength transmitted through the tissue sample and detected by the two or more detectors, and generating a time-series signal of the decay time of the intensity autocorrelation function;
   obtaining a power spectrum of the time-series signal and detecting peaks of the power spectrum using a spectrum analyzer; and
   processing, using a processor, electrical signals output from the two or more detectors to quantify the intensity of the light of first wavelength and the intensity of the light of second wavelength transmitted through the tissue sample, and processing one electrical signal output from one the two or more detectors to quantify the temporal intensity fluctuations in one of the light of first wavelength and the light of second wavelength transmitted through the tissue sample,
   wherein the processor synchronizes the intensity of the light of first wavelength and the intensity of the light of second wavelength based on the peaks of the power spectrum which correspond to peak intensities of the temporal intensity fluctuations of the one of the light of first wavelength and the light of second wavelength, and
   wherein, based on the synchronized intensity of the light of first wavelength and the intensity of the light of second wavelength transmitted through the tissue sample, the processor calculates one or more of an oxygen saturation value, and a blood flow value within the tissue sample.

14. The method according to claim 13, further comprising:
   irradiating the tissue sample with the light of first wavelength and the light of second wavelength via a light delivering optical system including an optical fiber having a distal end thereof in physical contact with the tissue sample, and a proximal end thereof connected to the two or more light sources via a coupler.

15. The method according to claim 13, further comprising:
   collecting the light of first wavelength and the light of second wavelength transmitted through the tissue sample via a light collecting optical system including a double clad fiber having a distal end thereof in physical contact with the tissue sample and a proximal end thereof in optical connection with the two or more detectors,
   wherein the double clad fiber includes a core, an inner cladding surrounding the core, and an outer cladding surrounding the inner cladding, and
   wherein, of the collected light, the light of first wavelength and the light of second wavelength are transmitted through both the core and the inner cladding of the double clad fiber.

16. The method according to claim 15, further comprising:
   selectively dividing the light of first wavelength from the light of second wavelength transmitted through the double clad fiber; and
   dividing the collected light which propagates in the core from the collected light which propagates in the inner cladding of the double clad fiber.

17. The method according to claim 13,
   wherein irradiating the tissue sample includes irradiating the tissue sample with a first light source emitting light of the first wavelength in a range between 600 nm to 800 nm, and a second light source emitting light of the second wavelength in a range between 800 nm to 1000 nm, and
   wherein a coherence length of the second light source at the second wavelength is equal to or longer than a coherence length of the first light source at the first wavelength.

18. The method according to claim 13,
   wherein irradiating the tissue sample with the two or more light sources includes irradiating the tissue sample with a first light source emitting light of the first wavelength in a range between 600 nm to 800 nm, a second light source emitting light of the second wavelength in a range between 800 nm to 1000 nm, and a third light source emitting a light of third wavelength which is an isosbestic wavelength of the tissue sample.

19. The method according to claim 13, further comprising:
   delivering the light from the two or more light sources to the sample via a first double clad fiber, wherein the light of first wavelength output from a first light source propagates in the core of the first double clad fiber, and the light of second wavelength output from a second light source propagates in the inner cladding of the first double clad fiber;
   collecting from the tissue sample light of the first wavelength and light of the second wavelength transmitted through the tissue sample via a second double clad fiber, wherein the second double clad fiber includes a core, an inner cladding surrounding the core, and an outer cladding surrounding the inner cladding, and
   wherein, of the collected light, the light of first wavelength and the light of second wavelength are transmitted through both the core and the inner cladding of the double clad fiber.

* * * * *